US009913571B2

(12) United States Patent
Obara et al.

(10) Patent No.: US 9,913,571 B2
(45) Date of Patent: Mar. 13, 2018

(54) ENDOSCOPE SYSTEM OF OBSERVING VARIOUS FIELD OF VIEW

(71) Applicant: OLYMPUS CORPORATION, Tokyo (JP)

(72) Inventors: Tatsuya Obara, Hachioji (JP); Takeshi Takahashi, Hachioji (JP); Takashi Ito, Fuchu (JP); Hideyuki Kugimiya, Hachioji (JP)

(73) Assignee: OLYMPOUS CORPORATION, Tokyo (JP)

( * ) Notice: Subject to any disclaimer, the term of this patent is extended or adjusted under 35 U.S.C. 154(b) by 0 days.

(21) Appl. No.: 15/281,655

(22) Filed: Sep. 30, 2016

(65) Prior Publication Data

US 2017/0014017 A1 Jan. 19, 2017

Related U.S. Application Data

(63) Continuation of application No. PCT/JP2015/059209, filed on Mar. 25, 2015.

(30) Foreign Application Priority Data

Mar. 31, 2014 (JP) ................ 2014-073512

(51) Int. Cl.
*A61B 1/04* (2006.01)
*A61B 1/005* (2006.01)
(Continued)

(52) U.S. Cl.
CPC .......... *A61B 1/0051* (2013.01); *A61B 1/0005* (2013.01); *A61B 1/00009* (2013.01);
(Continued)

(58) Field of Classification Search
CPC ............ A61B 1/00043; A61B 1/00009; A61B 1/0005; A61B 1/00045; A61B 1/00181;
(Continued)

(56) References Cited

U.S. PATENT DOCUMENTS 9,615,772 B2* 4/2017 Hale .................. A61B 1/00009
2005/0033117 A1 2/2005 Ozaki et al.
(Continued)

FOREIGN PATENT DOCUMENTS

EP 2 380 483 A1 10/2011
EP 2 762 059 A1 8/2014
(Continued)

OTHER PUBLICATIONS

Japanese Office Action dated Mar. 1, 2016 issued in corresponding Japanese Patent Application No. 2015-552955.
(Continued)

*Primary Examiner* — John P Leubecker
(74) *Attorney, Agent, or Firm* — Scully, Scott, Murphy & Presser, P.C.

(57) ABSTRACT

An endoscope system includes: an insertion portion inserted into a subject; a forward image pickup device configured to acquire a first subject image from a first direction; an image pickup device configured to acquire a second subject image from a second direction; and an image processing section configured to generate a bird's-eye view image based on a bird's-eye view subject image looking down on the subject from a virtual point of view away from the insertion portion and configured to execute a process of associating the first subject image and the first direction in the bird's-eye view subject image and associating the second subject image and the second direction in the bird's-eye view subject image.

8 Claims, 21 Drawing Sheets

(51) Int. Cl.
*A61B 1/00* (2006.01)
*A61B 1/12* (2006.01)
*G02B 23/24* (2006.01)
*A61B 1/015* (2006.01)
*A61B 1/018* (2006.01)

(52) U.S. Cl.
CPC ...... *A61B 1/00091* (2013.01); *A61B 1/00181* (2013.01); *A61B 1/015* (2013.01); *A61B 1/018* (2013.01); *A61B 1/12* (2013.01); *A61B 1/126* (2013.01); *G02B 23/2484* (2013.01)

(58) Field of Classification Search
CPC ... A61B 1/00177; A61B 5/743; A61B 5/7425; A61B 2090/364; A61B 2090/371
See application file for complete search history.

(56) References Cited

U.S. PATENT DOCUMENTS

| | | |
|---|---|---|
| 2010/0249506 A1 | 9/2010 | Prisco |
| 2011/0085021 A1* | 4/2011 | Wang ............... A61B 1/00009 348/36 |
| 2011/0275889 A1 | 11/2011 | Kase et al. |
| 2011/0282148 A1 | 11/2011 | Kase et al. |
| 2012/0086771 A1* | 4/2012 | Wang ............... A61B 1/00009 348/36 |
| 2013/0217962 A1* | 8/2013 | Date ............... A61B 1/00009 600/103 |
| 2014/0005484 A1* | 1/2014 | Charles ............... A61B 17/02 600/201 |
| 2014/0012081 A1* | 1/2014 | Juergens ............ A61B 1/00181 600/109 |
| 2014/0204187 A1 | 7/2014 | Sasaki et al. |
| 2014/0333743 A1* | 11/2014 | Gilreath ............ A61B 1/00009 348/74 |
| 2016/0015258 A1* | 1/2016 | Levin ............... A61B 1/00006 600/109 |

FOREIGN PATENT DOCUMENTS

| | | |
|---|---|---|
| JP | 3337682 B | 10/2002 |
| JP | 2005-338551 A | 12/2005 |
| JP | 2010-279539 A | 12/2010 |
| JP | 2013-66646 A | 4/2013 |
| JP | 2013-542467 A | 11/2013 |
| WO | WO 2011/055640 A1 | 12/2011 |
| WO | WO 2012/056453 A2 | 5/2012 |

OTHER PUBLICATIONS

International Search Report dated Jun. 23, 2015 issued in corresponding International Patent Application No. PCT/JP2015/059209.
European Search Report dated Sep. 8, 2017 issued in European Application No. 15773861.8.

* cited by examiner (Prior Art)

ENDOSCOPE SYSTEM OF OBSERVING VARIOUS FIELD OF VIEW

CROSS REFERENCE TO RELATED APPLICATION

This application is a continuation application of PCT/JP2015/059209 filed on Mar. 25, 2015 and claims benefit of Japanese Application No. 2014-073512 filed in Japan on Mar. 31, 2014, the entire contents of which are incorporated herein by this reference.

BACKGROUND OF THE INVENTION

1. Field of the Invention

The present invention relates to an endoscope system, and particularly, to an endoscope system capable of independently and simultaneously observing a forward field of view and a lateral field of view.

2. Description of the Related Art

An endoscope system is widely used in a medical field, an industrial field, and the like, the endoscope system including: an endoscope configured to pick up an image of a subject inside of a lumen such as a body cavity; an image processing apparatus configured to generate observation images of the subject picked up by the endoscope; and the like.

For example, Japanese Patent No. 3337682 discloses a wide-angle endoscope system including an endoscope, in which a forward observation lens configured to acquire a forward field of view image is provided on a distal end surface of a distal end portion of an insertion portion, and a plurality of lateral observation lenses configured to acquire lateral field of view images are provided in a circumferential direction of the distal end portion. Image pickup devices are further provided at respective image formation positions of the forward observation lens and the plurality of lateral observation lenses, and the image pickup devices pick up a forward field of view image and a plurality of lateral field of view images.

The wide-angle endoscope system is configured to independently obtain the forward field of view image and the plurality of lateral field of view images and is configured to display the independent images on one display means.

More specifically, when the images picked up by the respective image pickup devices are displayed on a monitor in the wide-angle endoscope system, the forward field of view image picked up by a forward observation image pickup device is arranged and displayed at a center, and the lateral field of view images picked up by a plurality of lateral observation image pickup devices, such as two lateral observation image pickup devices, are arranged and displayed on both sides of the forward field of view image, respectively.

By the way, in the wide-angle endoscope system described in Japanese Patent No. 3337682, a forward field of view image 516A picked up by the forward observation image pickup device is arranged and displayed at a center in a monitor screen 535 shown in FIG. 26, and lateral field of view images 516B and 516C picked up by the two lateral observation image pickup devices are arranged and displayed on both sides of the forward field of view image 516A, for example.

Note that in FIG. 26, it is assumed that "↑", "☆", and "◇" are schematically picked up for the forward field of view image 516A and the two lateral field of view images 516B and 516C, respectively.

Whether the forward field of view image 516A and the two lateral field of view images 516B and 516C (schematically illustrated by "↑", "☆", and "◇", respectively) indicate directions and ranges corresponding to 517a, 517b, and 517c in FIG. 27a, respectively, or indicate positions and ranges corresponding to 517a', 517b', and 517c' in FIG. 27b, respectively, is not clearly recognized. Note that reference signs 517d and 517d' schematically illustrate an insertion portion distal end portion of the endoscope in FIGS. 27a and 27b, and a right direction corresponds to a forward direction of the insertion portion in FIGS. 27a and 27b.

That is, as shown for example in FIG. 28, in an endoscope including one image pickup optical system and including only one display screen 416 displayed on a monitor screen 435, even when "↑", "☆", and "◇" are respectively lined up and displayed on the display screen (see left side in FIG. 28), directions and ranges of the images relative to the endoscope can be accurately imagined as indicated by reference sign 417 on a right side of FIG. 28.

SUMMARY OF THE INVENTION

An aspect of the present invention provides an endoscope system including: an insertion portion inserted into a subject in a longitudinal axis direction; a first subject image acquisition section provided on the insertion portion and configured to acquire a first subject image from a first region of the subject; a second subject image acquisition section provided on the insertion portion and configured to acquire a second subject image from a second region of the subject different from the first region; a first image signal generation section configured to generate a first image signal based on an endoscopic subject image including the first subject image and the second subject image; a second image signal generation section configured to generate a second image signal based on a schematic diagram of the insertion portion and an array of the first and second regions relative to the insertion portion; an image processing section configured to associate the first subject image and the first region with respect to the schematic diagram of the insertion portion, associate the second subject image and the second region with respect to the schematic diagram of the insertion portion, and synthesize the first and second image signals to arrange the associated first subject image and the associated second subject image on a screen; and an image signal output section configured to generate an output image signal for display on the screen based on the first and second image signals synthesized by the image processing section.

DETAILED DESCRIPTION OF THE PREFERRED EMBODIMENT(S)

Hereinafter, embodiments of the present invention will be described with reference to the drawings.

First Embodiment

Figure 1:
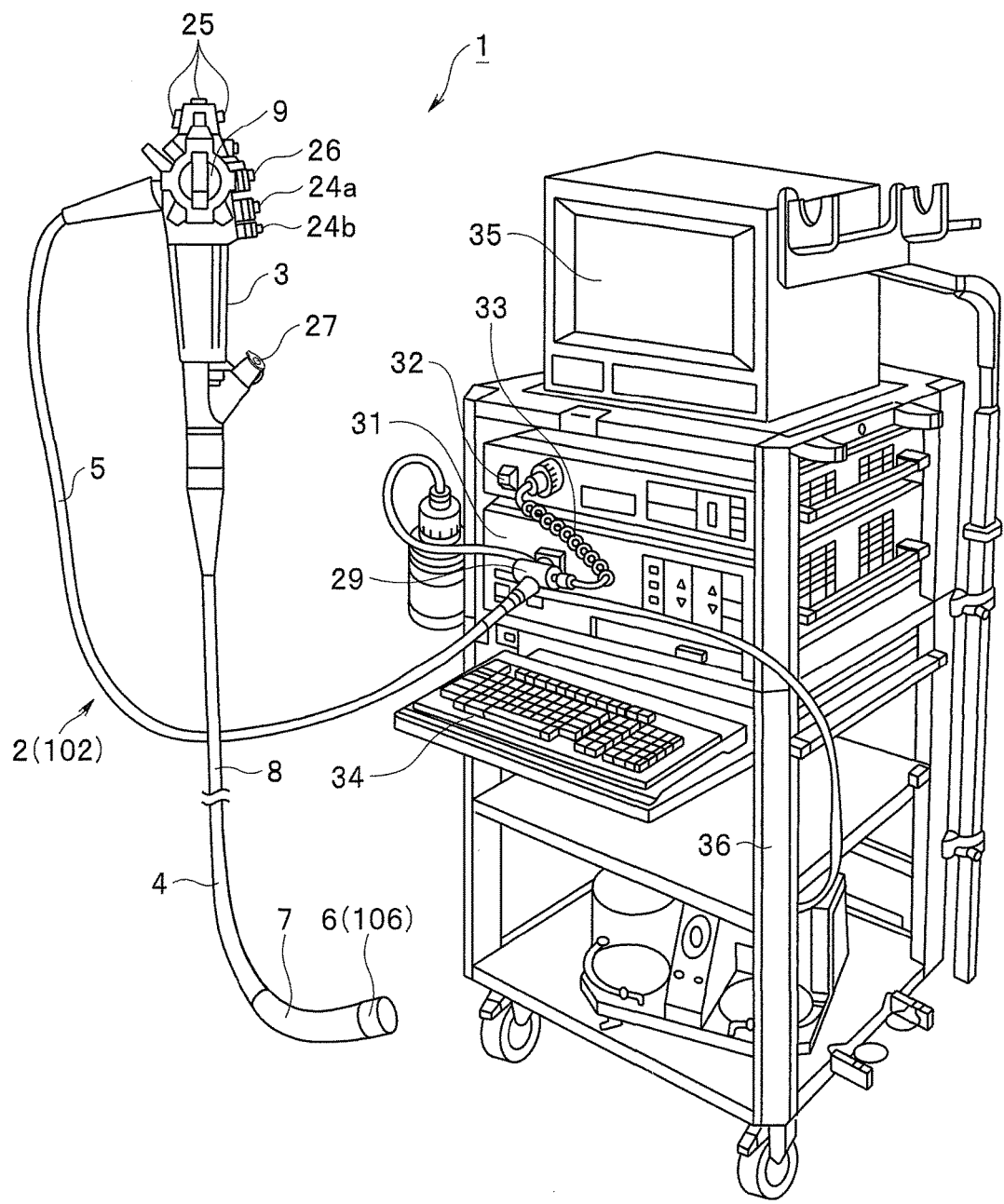
FIG. 1 is a diagram showing a configuration of an endoscope system of a first embodiment of the present invention.
Figure 2:
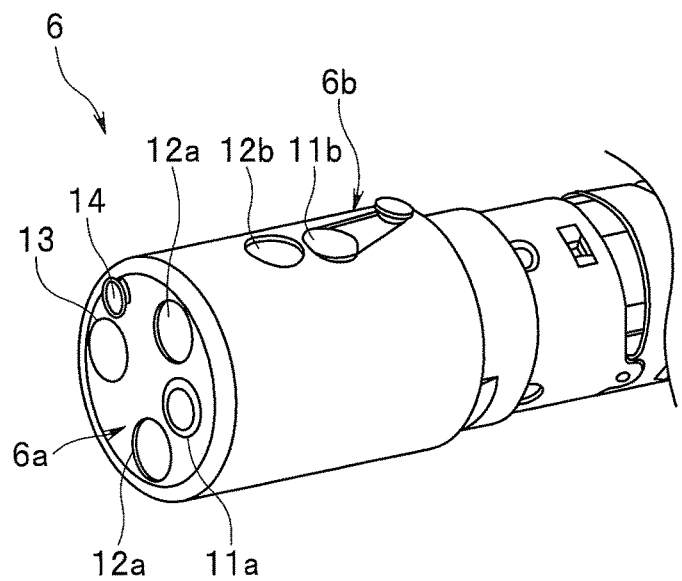
FIG. 2 is a perspective view showing a configuration of an insertion portion distal end portion in the endoscope system of the first embodiment.
Figure 3:
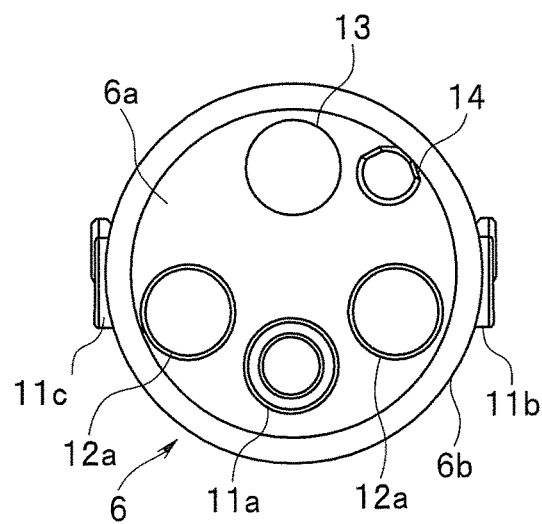
FIG. 3 is a front view showing a distal end of the insertion portion distal end portion in the endoscope system of the first embodiment.

A configuration of an endoscope system of a first embodiment will be described with reference to FIGS. 1 to 3. FIG. 1 is a diagram showing a configuration of an endoscope system of the first embodiment of the present invention. FIG. 2 is a perspective view showing a configuration of an insertion portion distal end portion in the endoscope system of the first embodiment. FIG. 3 is a front view showing a distal end of the insertion portion distal end portion in the endoscope system of the first embodiment.

As shown in FIG. 1, an endoscope system 1 includes: an endoscope 2 configured to pick up an image of an object to be observed and output an image pickup signal; a light source apparatus 31 configured to supply illuminating light configured to illuminate the object to be observed (subject); a video processor 32 configured to generate and output a video signal according to the image pickup signal; and a monitor 35 configured to display an observation image according to the video signal.

The endoscope 2 includes: an operation portion 3 for an operator to grasp and operate; an elongated insertion portion 4 formed on a distal end side of the operation portion 3 and inserted into a body cavity or the like; and a universal cord 5 with one of end portions provided to extend from a side portion of the operation portion 3.

The endoscope 2 of the present embodiment is a wide-angle endoscope capable of observing a field of view equal to or greater than 180 degrees, and the endoscope 2 realizes prevention of missing of a lesion at a location that is hard to view just by observation in a forward direction in a body cavity, particularly, in a large intestine, such as backside of folds and boundary of organs. In inserting the insertion portion 4 of the endoscope 2 into the large intestine, motions occur as in a normal colonoscope, such as twisting and back and forth movement of the insertion portion 4 and hooking of an intestinal wall for temporary fixation.

The insertion portion 4 includes: a rigid distal end portion 6 provided closest to a distal end; a bendable bending portion 7 provided at a back end of the distal end portion 6; and a long flexible tube portion 8 with flexibility provided at a back end of the bending portion 7. The bending portion 7 performs a bending motion according to operation of a bending operation lever 9 provided on the operation portion 3.

On the other hand, as shown in FIGS. 2 and 3, a forward observation window 11a for observation in a forward field of view direction is arranged on a distal end surface of the distal end portion 6 of the endoscope 2, and a plurality of lateral observation windows 11b and 11c for observation in a lateral field of view direction are arranged on a side surface 6b of the distal end portion 6 of the endoscope 2.

The lateral observation windows 11b and 11c are disposed at equal intervals, for example, intervals of 180 degrees, in a circumferential direction of the distal end portion 6 and are disposed to face substantially right and left directions, respectively, relative to the forward observation window 11a.

Note that in the present embodiment, the number of lateral observation windows 11b and 11c arranged at equal intervals in the circumferential direction of a distal end portion 6a is not limited to two. For example, one side-view observation window may be arranged, or three or more lateral observation windows may be arranged. Examples of arranging three or more lateral observation windows include arranging the side-view observation window every 120 degrees in the circumferential direction and arranging the side-view observation window every 90 degrees in the circumferential direction.

On the distal end surface of the distal end portion 6 of the endoscope 2, two forward illuminating windows 12a configured to emit illuminating light in a range of the forward field of view of the forward observation window 11a are arranged at positions adjacent to the forward observation window 11a. On the side surface 6b of the distal end portion 6 of the endoscope 2, lateral illuminating windows 12b and 12c (not shown) configured to emit illuminating light to a range of the lateral field of view of the lateral observation windows 11b and 11c are disposed at positions adjacent to the lateral observation windows 11b and 11c, respectively.

The distal end surface of the distal end portion 6 of the endoscope 2 is provided with: a distal end opening portion 13 communicating with a treatment instrument channel not shown formed by a tube and the like disposed in the insertion portion 4, the distal end opening portion 13 capable of causing a treatment instrument (distal end portion of the treatment instrument) inserted into the treatment instrument channel to protrude; and a forward observation window nozzle portion 14 configured to inject air or liquid for cleaning the forward observation window 11a.

On the side surface of the distal end portion 6 of the endoscope 2, lateral observation window nozzle portions not shown configured to inject air or liquid for cleaning the lateral observation windows 11b and 11c are provided adjacent to the lateral observation windows 11b and 11c, respectively.

Returning to FIG. 1, the operation portion 3 is provided with: an air/liquid feeding operation button 24a capable of instructing operation for injecting the air or the liquid for cleaning the forward observation window 11a from the forward observation window nozzle portion 14; and an air/liquid feeding operation button 24b capable of instructing operation for injecting the air or the liquid for cleaning the lateral observation windows 11b and 11c from the lateral observation window nozzle portions not shown. The air/liquid feeding operation buttons 24a and 24b can be pressed to switch air feeding and liquid feeding.

Although a plurality of air/liquid feeding operation buttons are provided to correspond to the respective nozzle portions in the present embodiment, the air or the liquid may be injected from both of the forward observation window nozzle portion 14 and the lateral observation window nozzle portions not shown by operation of one air/liquid feeding operation button, for example.

A plurality of scope switches 25 are further provided on a top portion of the operation portion 3. The scope switches 25 are configured to allow allocating functions of respective switches so as to be able to output various described signals corresponding to ON, OFF, and the like that can be used in the endoscope 2. More specifically, functions for outputting signals corresponding to start and stop of forward water feeding, execution and cancellation of freezing, notification of a use state of the treatment instrument, and the like can be allocated to the scope switches 25 as functions of the respective switches.

Note that in the present embodiment, the functions of at least one of the air/liquid feeding operation buttons 24a and 24b may be allocated to one of the scope switches 25.

A suction operation button 26 that allows instructing a suction unit or the like not shown to suck and recover a mucus or the like in a body cavity from the distal end opening portion 13 is disposed on the operation portion 3.

The mucus or the like in the body cavity sucked according to the motion of the suction unit or the like not shown is recovered in a suction bottle or the like of the suction unit not shown through the distal end opening portion 13, the treatment instrument channel not shown in the insertion portion 4, and a treatment instrument insertion port 27 provided near a front end of the operation portion 3.

The treatment instrument insertion port 27 communicates with the treatment instrument channel not shown in the insertion portion 4 and is formed as an opening that allows inserting the treatment instrument not shown. That is, the operator can insert the treatment instrument from the treatment instrument insertion port 27 and cause a distal end side of the treatment instrument to protrude from the distal end opening portion 13 to thereby perform a treatment using the treatment instrument.

On the other hand, as shown in FIG. 1, a connector 29 that can be connected to the light source apparatus 31 is provided on the other end portion of the universal cord 5.

A distal end portion of the connector 29 is provided with: a pipe sleeve (not shown) serving as a connection end portion of a fluid conduit; and a light guide pipe sleeve (not shown) serving as a supply end portion of the illuminating light. An electrical contact portion (not shown) that allows connecting one of end portions of a connection cable 33 is provided on a side surface of the connector 29. A connector for electrically connecting the endoscope 2 and the video processor 32 is further provided on the other end portion of the connection cable 33.

Note that a scope ID 29a storing unique predetermined ID information in the endoscope 2 is disposed on the connector 29 (details will be described later).

A plurality of signal lines for transferring various electrical signals and a light guide for transferring the illuminating light supplied from the light source apparatus 31 are bundled and embedded in the universal cord 5.

On the other hand, an end portion on a light emission side of the light guide embedded from the insertion portion 4 to the universal cord 5 is branched near the insertion portion 4, and respective light emission end surfaces are arranged on the forward illuminating windows 12a and the lateral illuminating windows 12b and 12c. An end portion on a light incident side of the light guide is arranged on the light guide pipe sleeve of the connector 29.

Note that in the means for illuminating the subject in the present first embodiment, the illuminating light supplied from the light source apparatus 31 is transferred by the light guide, and the illuminating light is emitted from each of the illuminating windows. However, the illumination means is not limited to this.

For example, light emitting elements, such as light emitting diodes (LEDs), may be provided inside of the forward illuminating windows 12*a*, the lateral illuminating window 12*b*, and the lateral illuminating window 12*c*, and light from the light emitting elements may be emitted from the respective illuminating windows.

The video processor 32 outputs drive signals for driving a plurality of image pickup devices provided on the distal end portion 6 of the endoscope 2. The video processor 32 applies signal processing to image pickup signals outputted from the plurality of image pickup devices to generate video signals and outputs the video signals to the monitor 35.

Although details will be described later, the video processor 32 arranges a forward field of view image acquired by the forward observation window 11*a* at a center and arranges two lateral field of view images acquired by the lateral observation windows 11*b* and 11*c* on the left and right of the forward field of view image. The video processor 32 applies predetermined image processing to the forward field of view image and the two lateral field of view images and outputs the images to the monitor 35.

Returning to FIG. 1, peripheral apparatuses, such as the light source apparatus 31, the video processor 32, and the monitor 35, are arranged on a stand 36 along with a keyboard 34 for, for example, inputting patient information.

Next, main parts of an electrical configuration in the endoscope system of the present first embodiment will be described.

Figure 4:
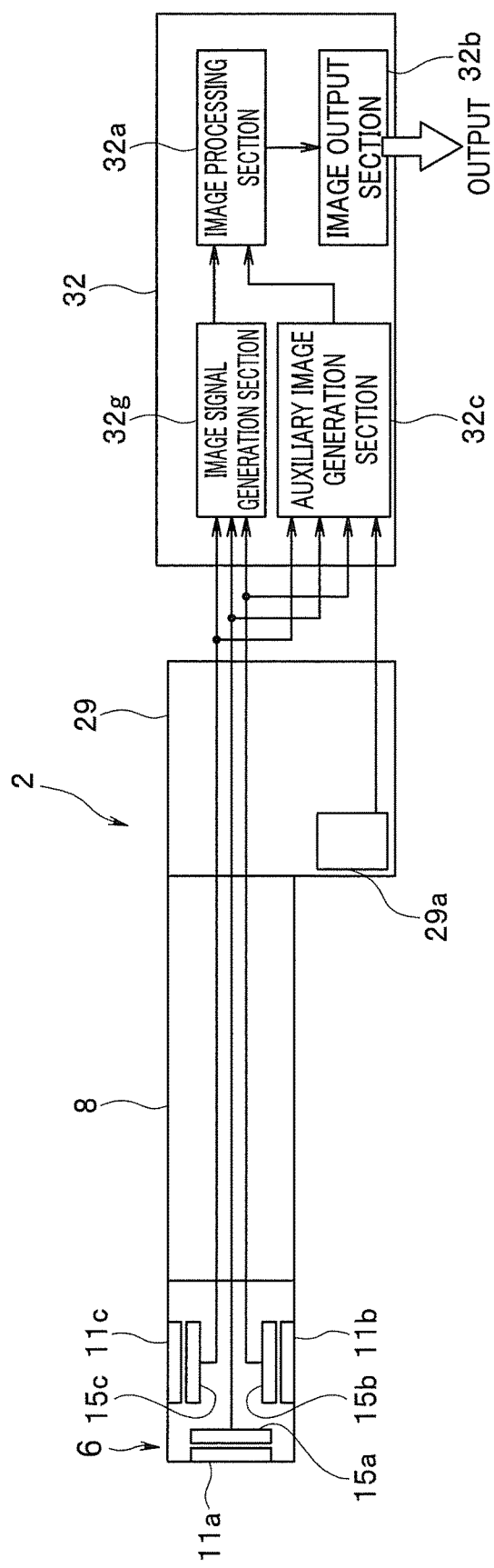
FIG. 4 is a block diagram showing main parts of an electrical configuration of an endoscope and a processor in the endoscope system of the first embodiment.

FIG. 4 is a block diagram showing main parts of an electrical configuration of the endoscope and the processor in the endoscope system of the first embodiment.

As shown in FIG. 4, the forward observation window 11*a* and a forward image pickup device 15*a* forming a first subject image acquisition section configured to observe a forward direction including the front substantially parallel to a longitudinal axis direction of the insertion portion 4, that is, a first region of the subject, are disposed on a front portion (distal end surface) in the distal end portion 6 of the insertion portion 4 of the endoscope 2 according to the present first embodiment.

The lateral observation windows 11*b* and 11*c* and lateral image pickup devices 15*b* and 15*c* forming a second subject image acquisition section configured to observe a lateral direction including a direction intersecting with the longitudinal axis direction of the insertion portion 4, that is, a second region of the subject, are disposed on a side portion (side surface) of the distal end portion 6.

The forward observation window 11*a* receives a first subject image from a forward direction (first direction; left side in FIG. 4 is forward), wherein a direction in the longitudinal axis direction of the insertion portion 4 in which the insertion portion 4 is inserted is the forward direction, that is, a front-view direction. The forward image pickup device 15*a* is arranged at an image formation position of the forward observation window 11*a* and an objective optical system not shown, and the forward image pickup device 15*a* photoelectrically converts the subject image received by the forward observation window 11*a*.

The lateral observation windows 11*b* and 11*c* receive a second subject image from a lateral direction that is a direction at least partially different from the forward direction (front-view direction or first direction) and that includes the circumferential direction of the distal end portion 6, that is, a side-view direction (second direction; illustrated as vertical direction in FIG. 4). The lateral image pickup devices 15*b* and 15*c* are arranged at image formation positions of respective objective optical systems not shown in the lateral observation windows 11*b* and 11*c*, and the lateral image pickup devices 15*b* and 15*c* photoelectrically convert a subject image received by the lateral observation window 11*b* or 11*c*.

The forward image pickup devices 15*a* to 15*c* are all electrically connected to an image signal generation section 32*g* described later and are configured to output an image pickup signal related to the forward field of view picked up by the forward image pickup device 15*a* and image pickup signals related to the lateral field of view respectively picked up by the lateral image pickup devices 15*b* and 15*c* to the image signal generation section 32*g* in the video processor 32.

The scope ID 29*a* storing unique predetermined ID information in the endoscope 2, such as information of view angle in the endoscope 2 in the present embodiment, is disposed on the connector 29 in the endoscope 2.

On the other hand, the video processor 32 outputs drive signals for driving the respective image pickup devices 15*a*, 15*b*, and 15*c*.

In addition, the video processor 32 includes: the image signal generation section (first image signal generation section) 32*g* configured to receive the image pickup signals from the respective image pickup devices 15*a*, 15*b*, and 15*c* to generate video signals (image signals) related to forward or lateral field of view; an image processing section 32*a* configured to apply predetermined image processing to the video signals (image signals); an image output section 32*b* configured to apply predetermined processing to the respective image signals processed by the image processing section 32*a* to generate output image signals to be outputted to the monitor 35 and output the output image signals; and an auxiliary image generation section (second image signal generation section) 32*c* configured to acquire the unique information in the endoscope 2 from the scope ID 29*a* in the connector 29 to generate a predetermined auxiliary image described later.

Next, image processing by the image processing section 32*a* and the auxiliary image generation section 32*c* in the present first embodiment will be described with reference to FIGS. 5 and 6.

Figure 5:
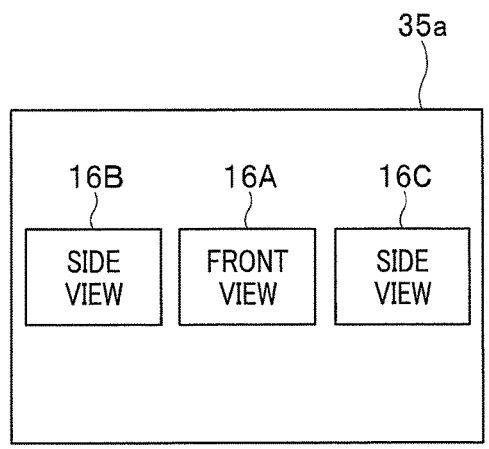
FIG. 5 is a diagram showing an outline of observation images displayed on a monitor screen in the endoscope system of the first embodiment.

FIG. 5 is a diagram showing an outline of observation images displayed on a monitor screen in the endoscope system of the first embodiment. FIG. 6 is a diagram showing an example of observation images displayed on the monitor screen in the endoscope system of the first embodiment.

As shown in FIG. 5, the image processing section 32*a* applies processing to arrange a forward field of view image 16A acquired by the first subject image acquisition section (the forward observation window 11*a*, the forward image pickup device 15*a*, and the like) at a center in a monitor screen 35*a* of the monitor 35 and to arrange and display two lateral field of view images 16B and 16C acquired by the second subject image acquisition section (the lateral observation windows 11*b* and 11*c*, the lateral image pickup devices 15*b* and 15*c*, and the like) on the left and right adjacent to the forward field of view image 16A. The image processing section 32a outputs the images to the image output section 32b.

More specifically, the image signal generation section 32g first receives the image pickup signals respectively outputted from the forward image pickup device 15a that is the first subject image acquisition section and the lateral image pickup devices 15b and 15c that are the second subject image acquisition section and generates image signals. The image processing section 32a applies predetermined image processing to the respective image signals to generate the forward field of view image 16A, the lateral field of view image 16B, and the lateral field of view image 16C, respectively.

Next, the image processing section 32a applies processing to arrange the forward field of view image 16A from the forward image pickup device 15a at the center of the monitor screen 35a and to arrange the two lateral field of view images 16B and 16C from the lateral image pickup devices 15b and 15c at adjacent left and right parts across the forward field of view image 16A on the monitor screen 35a.

The image processing section 32a further executes processing to display a frame portion (forward field of view image frame 16a) of the forward field of view image 16A and frame portions (lateral field of view image frames 16b and 16c) of the lateral field of view images 16B and 16C by using different colors (blue and red in the present embodiment) to distinguish the forward field of view and the lateral field of view.

That is, the use of different colors functions as an indicator for distinguishing the forward field of view and the lateral field of view. Note that in FIG. 6, horizontal lines in the frames indicate blue, and vertical lines indicate red.

Subsequently, the image processing section 32a outputs, toward the image output section 32b, image signals (first image signals) regarding the forward field of view image 16A, the lateral field of view image 16B, and the lateral field of view image 16C as well as the forward field of view image frame 16a, the lateral field of view image frame 16b, and the lateral field of view image frame 16c generated in the procedure described above.

Figure 6:
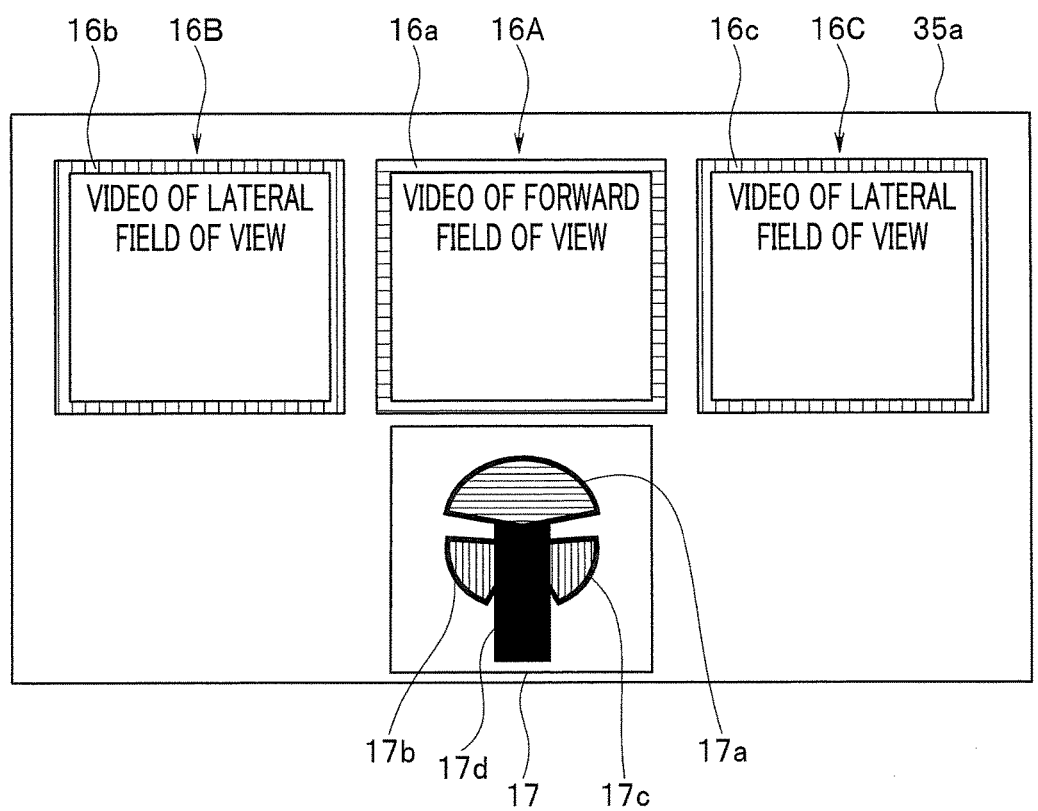
FIG. 6 is a diagram showing an example of observation images displayed on the monitor screen in the endoscope system of the first embodiment.

On the other hand, as shown in FIG. 6, the auxiliary image generation section 32c executes processing to read view angle information as unique ID information in the endoscope 2 stored in the scope ID 29a disposed on the connector 29, generate a bird's-eye view image 17 based on the read view angle information, and arrange and display the bird's-eye view image 17 on a lower part adjacent to the forward field of view image 16A in the monitor screen 35a.

The bird's-eye view image 17 is a bird's-eye view subject image, looking down on the subject from a virtual point of view away from the insertion portion 4 (for example, a point set in a direction intersecting with the longitudinal axis of the insertion portion, such as upper part of the endoscope insertion portion).

In the present embodiment, the bird's-eye view image 17 includes: a bird's-eye view insertion portion 17d illustrating a schematic diagram of a virtual insertion portion 4; a bird's-eye view forward field of view range 17a corresponding to the forward field of view image 16A arranged near the bird's-eye view insertion portion 17d; and bird's-eye view lateral field of view ranges 17b and 17c similarly arranged near the bird's-eye view insertion portion 17d and corresponding to the lateral field of view images 16B and 16C. On the monitor screen 35a, a state of array of the region regarding the forward field of view and the regions regarding the lateral field of view with respect to the virtual insertion portion is arranged and displayed on a lower part adjacent to the forward field of view image 16A.

The bird's-eye view forward field of view range 17a, the bird's-eye view lateral field of view range 17b, and the bird's-eye view lateral field of view range 17c are schematic diagrams showing forward and two lateral view angles, respectively, and are generated by the auxiliary image generation section 32c based on the view angle information in the endoscope 2 stored in the scope ID 29a.

In the present first embodiment, the auxiliary image generation section 32c further displays the bird's-eye view forward field of view range 17a and the bird's-eye view lateral field of view ranges 17b and 17c by using different colors in order to distinguish the bird's-eye view forward field of view range 17a, the bird's-eye view lateral field of view range 17b, and the bird's-eye view lateral field of view range 17c as an image regarding the forward field of view and images regarding the lateral field of view, respectively.

In the present first embodiment, the bird's-eye view forward field of view range 17a is associated with the forward field of view image 16A and is colored in blue (indicated by horizontal lines indicating the blue color in FIG. 6) that is the same as the forward field of view image frame 16a in the forward field of view image 16A. On the other hand, the bird's-eye view lateral field of view ranges 17b and 17c are similarly colored in red (indicated by vertical lines indicating the blue color in FIG. 6) that is the same as the lateral field of view image frames 16b and 16c in the lateral field of view images 16B and 16C.

The auxiliary image generation section 32c generates the bird's-eye view image 17 in the procedure described above, generates an image signal (second image signal) regarding the bird's-eye view image 17, and outputs the second image signal toward the image processing section 32a.

The image processing section 32a synthesizes the images based on the image signals (first image signals) generated by the image signal generation section 32g and the image signal (second image signal) generated by the auxiliary image generation section 32c and outputs the signals to the image output section 32b. The image output section 32b generates an output image signal for display on the monitor screen 35a and outputs the output image signal toward the monitor 35.

In this way, in the present first embodiment, the forward field of view image and the lateral field of view images as well as the bird's-eye view forward field of view range and the bird's-eye view lateral field of view ranges are distinguished by using different colors, respectively. The "forward field of view image" and the "bird's-eye view forward field of view range" as well as the "lateral field of view images" and the "bird's-eye view lateral field of view ranges" are "associated" and displayed in the same colors, respectively. The "use of different colors" is adopted as an indicator of the "association".

As described, the endoscope system of the present embodiment attains an effect of allowing to provide an endoscope system capable of independently and simultaneously observing the forward field of view and the lateral field of view, the endoscope system being capable of distinguishing and displaying the forward field of view image and the lateral field of view images and accurately recognizing the directions and the ranges in the subject that the forward field of view image and the lateral field of view images correspond.

First Modification of First Embodiment

Next, a first modification of the present first embodiment will be described.

Figure 7:
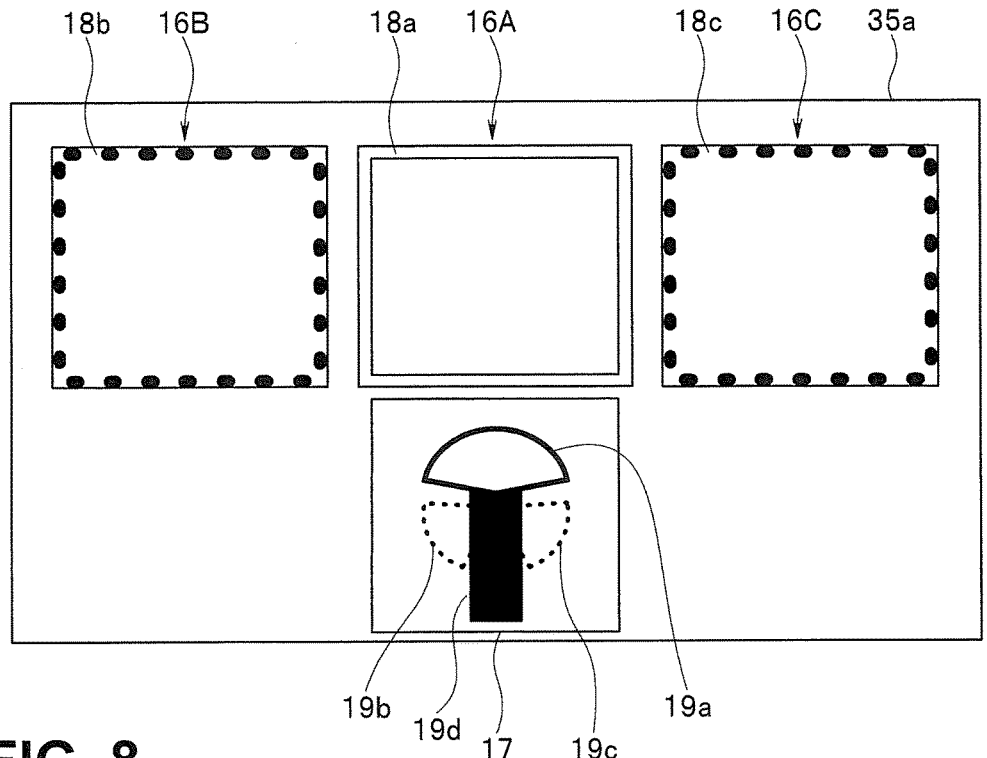
FIG. 7 is a diagram showing an example of observation images displayed on the monitor screen in a first modification of the endoscope system of the first embodiment.

FIG. 7 is a diagram showing an example of observation images displayed on the monitor screen in the first modification of the endoscope system of the first embodiment.

Although the "use of different colors" is adopted as an indicator of the "association" of the "forward field of view image" and the "bird's-eye view forward field of view range" as well as the "lateral field of view images" and the "bird's-eye view lateral field of view ranges" in the first embodiment, "use of different patterns with contour lines" for respective images is adopted as an indicator of the "association" in the first modification.

As shown in FIG. 7, contour lines of both of a forward field of view image frame 18a regarding the forward field of view image 16A and a bird's-eye view forward field of view range 19a in the bird's-eye view image 17 are indicated by solid lines in the present first modification. On the other hand, contour lines of both of lateral field of view image frames 18b and 18c regarding the lateral field of view images 16B and 16C arranged near a bird's-eye view insertion portion 19d indicating a schematic diagram of a virtual insertion portion 4 and bird's-eye view lateral field of view ranges 19b and 19c in the bird's-eye view image 17 are indicated by dashed lines.

In this way, the "association" of the "forward field of view image" and the "bird's-eye view forward field of view range" as well as the "lateral field of view images" and the "bird's-eye view lateral field of view ranges" is realized in the present first modification by "using different patterns with contour lines" for the respective images.

As described, the same effect as in the first embodiment can also be attained by the first modification in the present first embodiment.

Second Modification of First Embodiment

Next, a second modification of the present first embodiment will be described.

Figure 8:
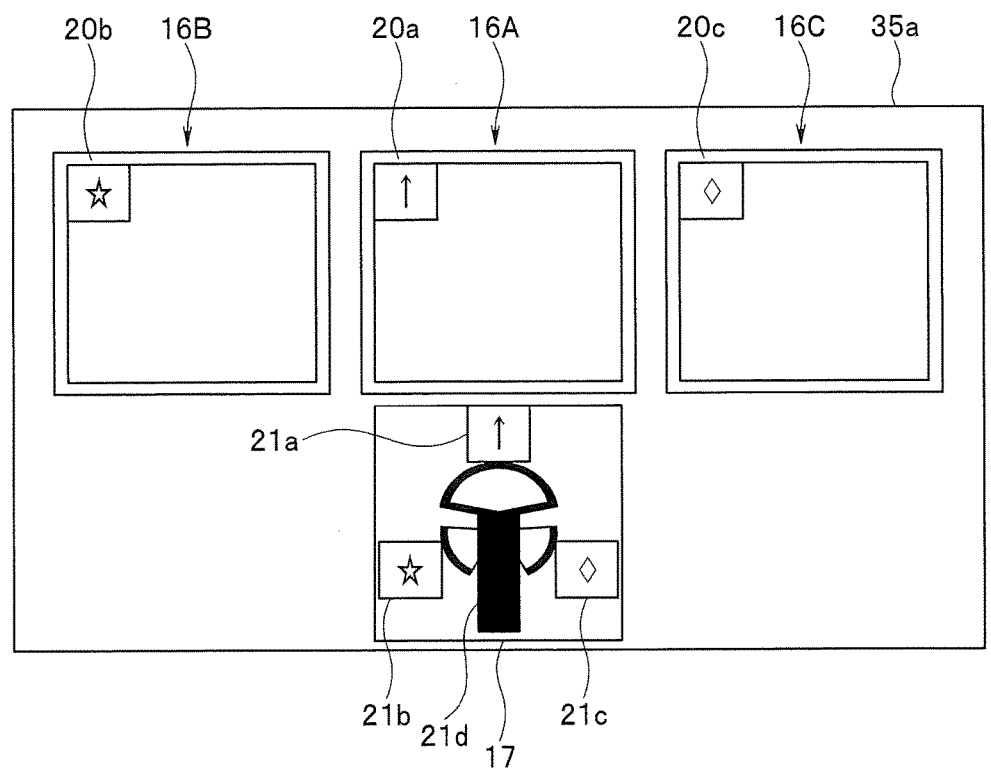
FIG. 8 is a diagram showing an example of observation images displayed on the monitor screen in a second modification of the endoscope system of the first embodiment.

FIG. 8 is a diagram showing an example of observation images displayed on the monitor screen in the second modification of the endoscope system of the first embodiment.

As described, although the "use of different colors" is adopted as an indicator of the "association" of the "forward field of view image" and the "bird's-eye view forward field of view range" as well as the "lateral field of view images" and the "bird's-eye view lateral field of view ranges" in the first embodiment, "use of different patterns with symbols" arranged on part of respective images is adopted as an indicator of the "association" in the second modification.

As shown in FIG. 8, a forward field of view image symbol 20a ("↑") is displayed on part of the forward field of view image 16A, and a symbol similar to the symbol 20a ("↑") is displayed near a bird's-eye view forward field of view range 21a in the bird's-eye view image 17 in the present second embodiment.

On the other hand, lateral field of view image symbols 20b ("☆") and 20c ("◇") are displayed on part of the lateral field of view images 16B and 16C, respectively, and symbols similar to the symbols 20b ("☆") and 20c ("◇") are displayed near bird's-eye view lateral field of view ranges 21b and 21c, respectively, arranged near a bird's-eye view insertion portion 21d indicating a schematic diagram of a virtual insertion portion 4 in the bird's-eye view image 17.

In this way, the "use of different patterns with symbols" arranged on part of the respective images realizes the "association" of the "forward field of view image" and the "bird's-eye view forward field of view range" as well as the "lateral field of view images" and the "bird's eye view lateral field of view ranges" in the present second embodiment.

As described, the same effect as in the first embodiment can also be attained by the second modification in the present first embodiment.

Third Modification of First Embodiment

Next, a third modification of the present first embodiment will be described.

Figure 9:
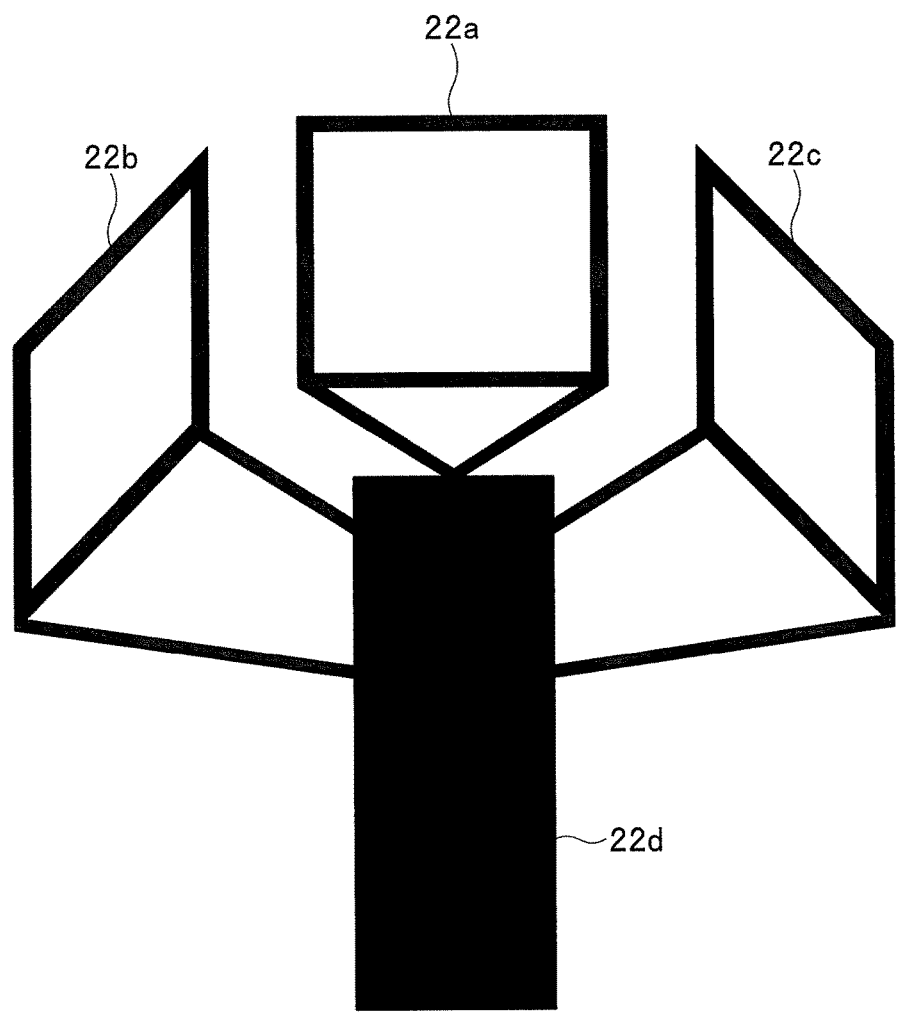
FIG. 9 is a diagram showing an example of bird's-eye view images displayed on the monitor screen in a third modification of the endoscope system of the first embodiment.

FIG. 9 is a diagram showing an example of a bird's-eye view image displayed on the monitor screen according to the third modification of the endoscope system of the first embodiment.

As shown in FIG. 9, parts equivalent to the bird's-eye view forward field of view range 17a and the bird's-eye view lateral field of view ranges 17b and 17c in the bird's-eye view image 17 of the first embodiment are replaced by a schematic diagram showing three-dimensional field of view ranges in the present third embodiment.

That is, three-dimensional bird's-eye view forward field of view range 22a, bird's-eye view lateral field of view range 22b, and bird's-eye view lateral field of view range 22c arranged near a bird's-eye view insertion portion 22d indicating a schematic diagram of a virtual insertion portion 4 as shown in FIG. 9 are displayed as bird's-eye view field of view ranges corresponding to the forward field of view image 16A, the lateral field of view image 16B, and the lateral field of view image 16C, respectively.

Obviously, the three-dimensional bird's-eye view forward field of view range 22a, bird's-eye view lateral field of view range 22b, and the bird's-eye view lateral field of view range 22c may be further provided with indicators for the "association" with the forward field of view image 16A and the lateral field of view images 16B and 16C by using different colors, using different patterns with contour lines, or using different patterns with symbols as in the first embodiment, the second modification of the first embodiment, and the third modification of the first embodiment.

In this way, the respective bird's-eye view field of view ranges in the bird's-eye view images can be three-dimensionally displayed in the present third modification to more accurately recognize the directions and the ranges in the subject that the forward field of view image and the lateral field of view images correspond.

As described, the same effect as in the first embodiment can also be attained by the third modification in the present first embodiment.

Fourth Modification of First Embodiment

Next, a fourth modification of the present first embodiment will be described.

Figure 10:
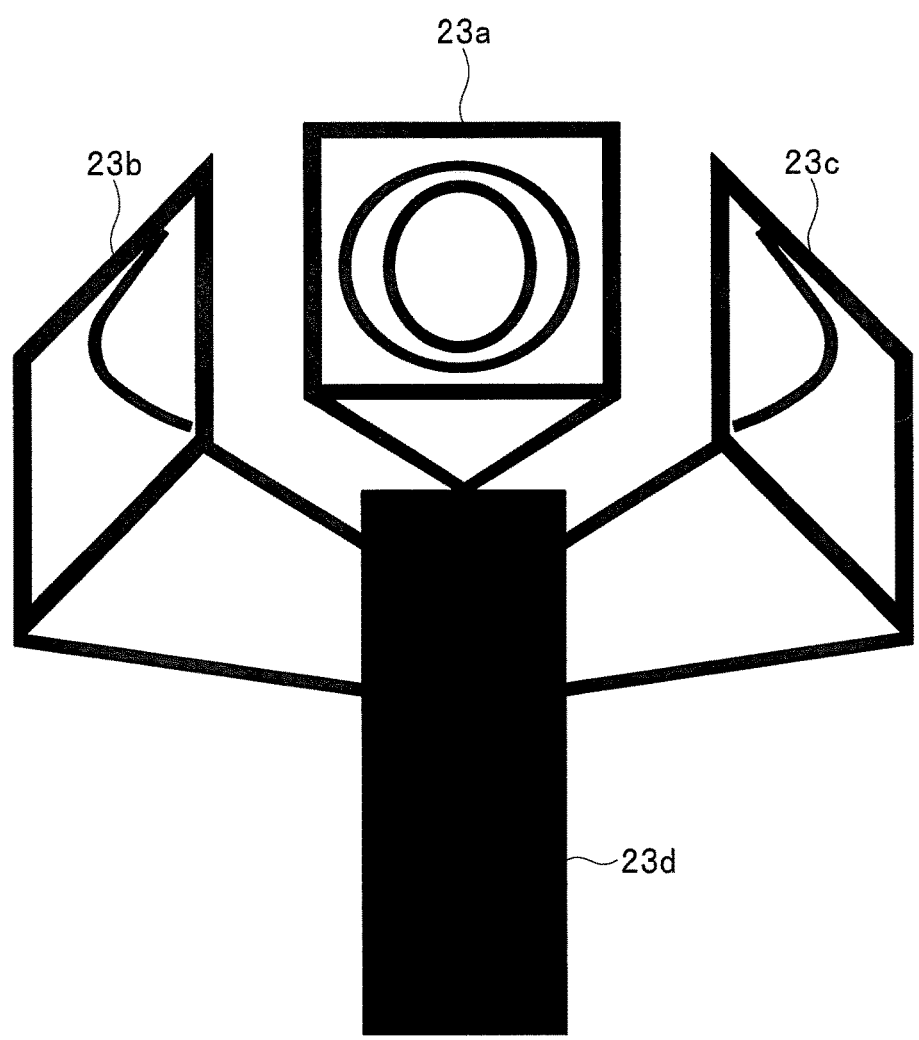
FIG. 10 is a diagram showing an example of bird's-eye view images displayed on the monitor screen in a fourth modification of the endoscope system of the first embodiment.

FIG. 10 is a diagram showing an example of a bird's-eye view image displayed on the monitor screen according to the fourth modification of the endoscope system of the first embodiment.

As shown in FIG. 10, in the present fourth modification, actual endoscopic images are displayed in the schematic diagram showing the respective three-dimensional bird's-eye view field of view ranges in the third modification.

That is, in the endoscope system of the present fourth modification, the image indicating the three-dimensional bird's-eye view forward field of view range 23a, bird's-eye view lateral field of view range 23b, and bird's-eye view lateral field of view range 23c respectively corresponding to the forward field of view image 16A, the lateral field of view image 16B, and the lateral field of view image 16C is arranged near the bird's-eye view insertion portion 19d indicating the schematic diagram of the virtual insertion portion 4 as in the third modification.

The auxiliary image generation section 32c uses the image pickup signals respectively outputted from the forward image pickup device 15a and the lateral image pickup devices 15b and 15c as shown in FIG. 4 to display endoscopic images regarding the respective forward field of view image 16A, lateral field of view image 16B, and lateral field of view image 16C in the images indicating the bird's-eye view forward field of view range 23a, the bird's-eye view lateral field of view range 23b, and the bird's-eye view lateral field of view range 23c.

In this way, the actual endoscopic images can be displayed in the schematic diagram showing the respective three-dimensional bird's-eye view field of view ranges in the bird's-eye view image to more accurately recognize the directions and the ranges in the subject that the forward field of view image and the lateral field of view images correspond in the present fourth modification.

As described, the same effect as in the first embodiment can also be attained by the fourth modification in the present first embodiment.

Furthermore, a following example will be illustrated as another application in the first embodiment and the first to fourth modifications of the first embodiment.

Figure 11:
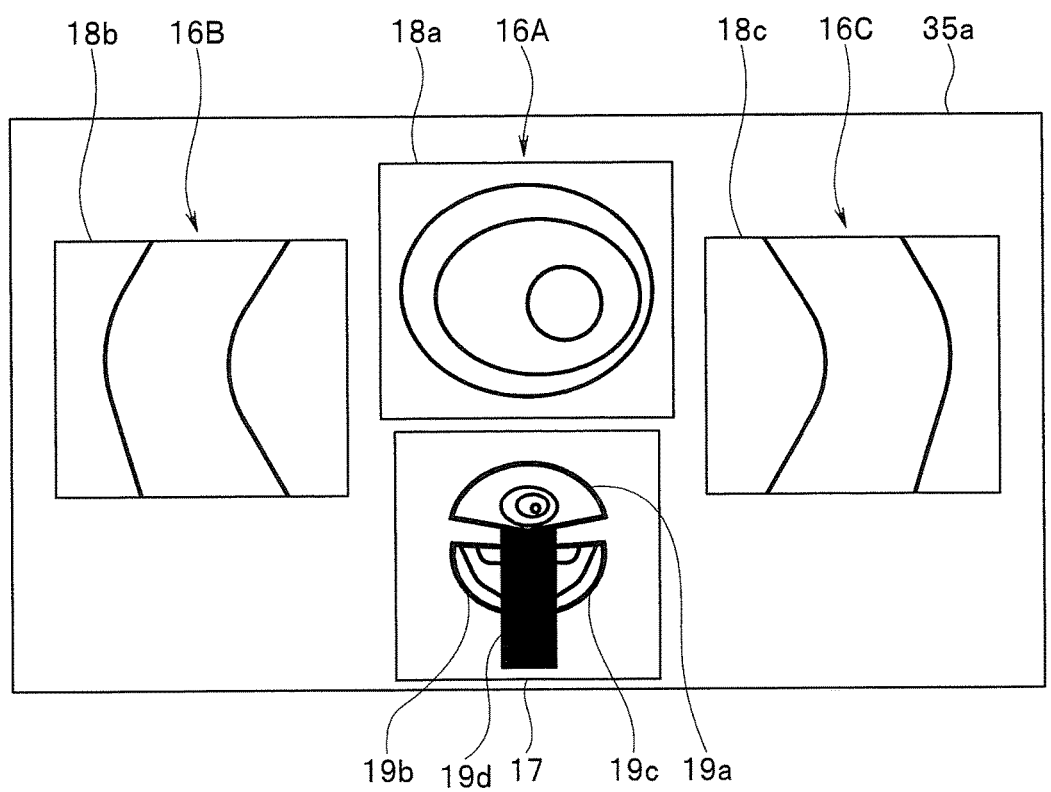
FIG. 11 is a diagram showing an example of observation images displayed on the monitor screen in another application of the endoscope system of the first embodiment.

As shown in FIG. 11, the image processing section 32a may adjust the positions of the display of the lateral field of view image 16B and the lateral field of view image 16C relative to the forward field of view image 16A to display the images in a display format similar to the array indicating the regions of the forward and lateral field of views with respect to the schematic diagram of the insertion portion of the bird's-eye view image 17.

Also, as shown in FIG. 11, the auxiliary image generation section 32c may use the image pickup signals respectively outputted from the forward image pickup device 15a and the lateral image pickup devices 15b and 15c to display the endoscopic images regarding the respective forward field of view image and two lateral field of view images as shown in FIG. 4 in the images indicating the bird's-eye view forward field of view range and the two bird's-eye view lateral field of view ranges, even in the display format of the bird's-eye view image 17 as in the first embodiment and the first and second modifications of the first embodiment.

Second Embodiment

Next, a second embodiment of the present invention will be described.

Although a basic configuration of an endoscope system according to the present second embodiment of the present invention is similar to that of the first embodiment as shown in FIG. 1, a configuration of the distal end portion of the insertion portion 4 in the endoscope 2 and image processing in the video processor 32 are different from those of the first embodiment.

Therefore, only the part different from the first embodiment will be described here, and the same part as in the first embodiment will not be described.

As shown in FIG. 1, an endoscope system 101 of the present second embodiment also includes, as in the first embodiment: an endoscope 102 configured to pick up an image of an object to be observed and output an image pickup signal; the light source apparatus 31 configured to supply illuminating light for illuminating the object to be observed; the video processor 32 configured to generate and output a video signal according to the image pickup signal; and a monitor 35 configured to display an observation image according to the video signal.

The endoscope 102 of the present second embodiment is also a wide-angle endoscope capable of observing a field of view equal to or greater than 180 degrees, and the endoscope 102 realizes prevention of missing of a lesion at a location that is hard to view just by observation in the forward direction in a body cavity, particularly, in a large intestine, such as backside of folds and boundary of organs.

In inserting the insertion portion 4 of the endoscope 102 into the large intestine, motions occur as in a normal colonoscope, such as twisting and back and forth movement of the insertion portion 4 and hooking of an intestinal wall for temporary fixation.

Figure 12:
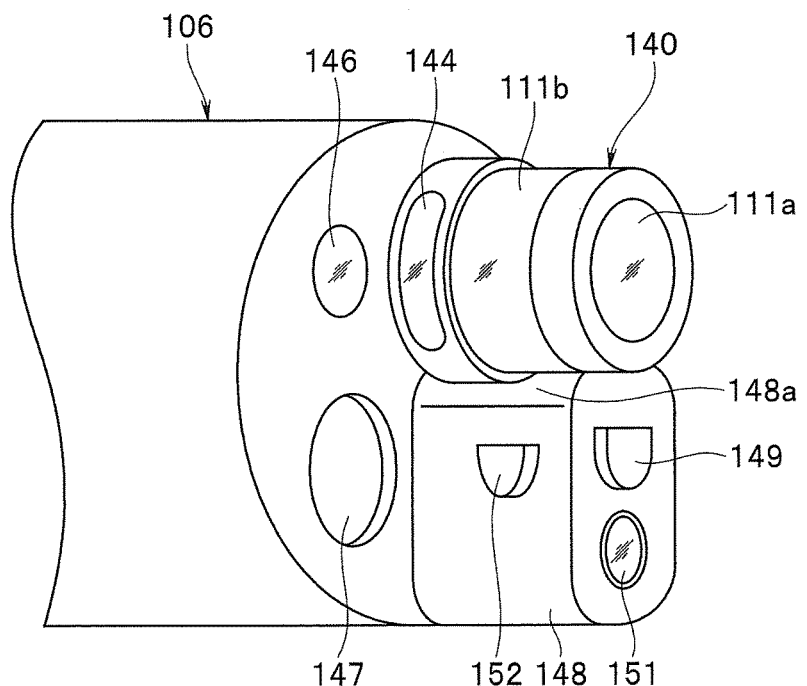
FIG. 12 is a perspective view showing a configuration of an insertion portion distal end portion in an endoscope system of a second embodiment of the present invention.
Figure 13:
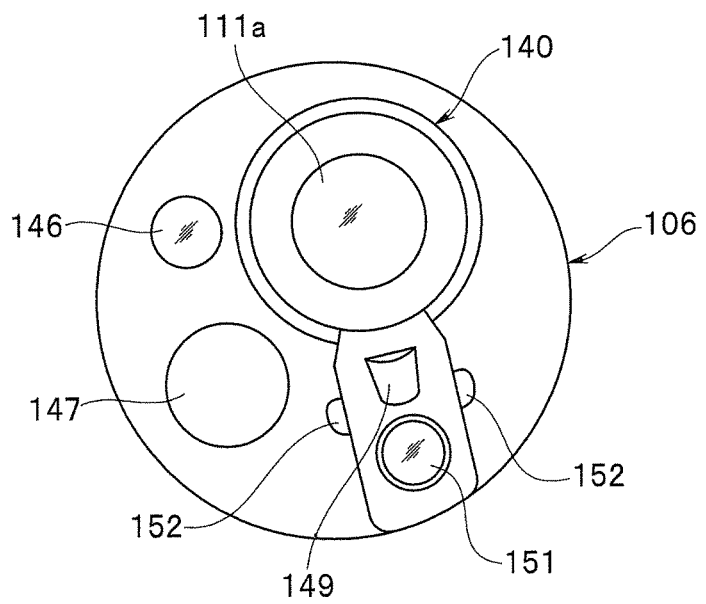
FIG. 13 is a front view showing a distal end of the insertion portion distal end portion in the endoscope system of the second embodiment.
Figure 14:
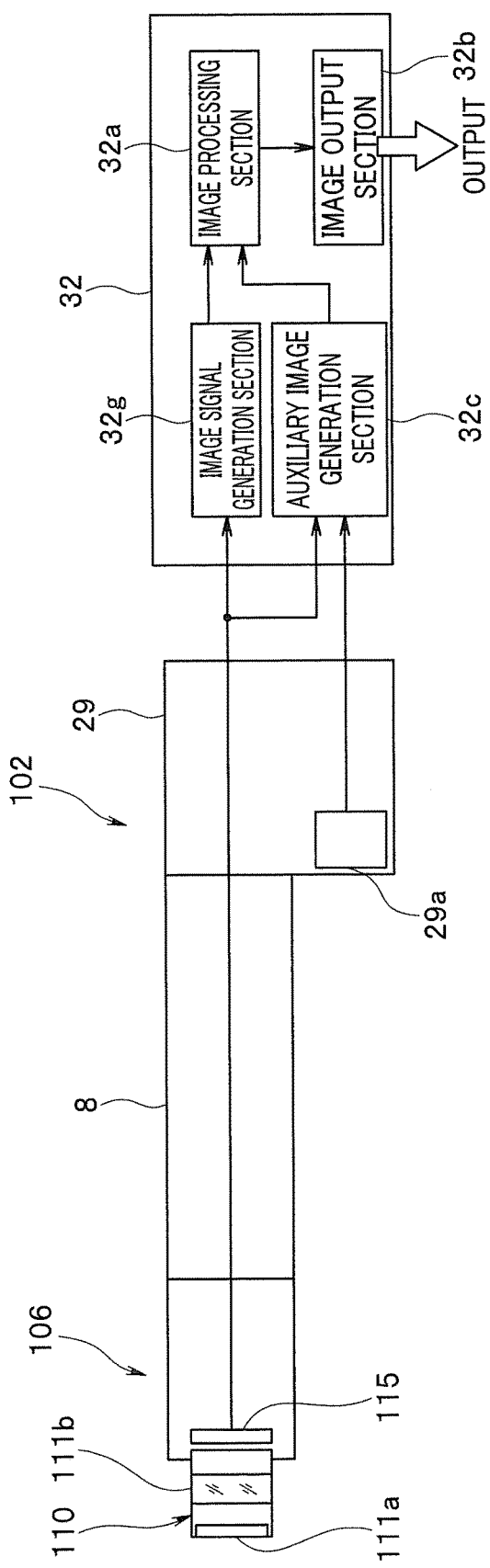
FIG. 14 is a block diagram showing an electrical configuration of main parts of an endoscope and the processor in the endoscope system of the second embodiment.

FIG. 12 is a perspective view showing a configuration of an insertion portion distal end portion in the endoscope system of the second embodiment of the present invention. FIG. 13 is a front view showing a distal end of the insertion portion distal end portion in the endoscope system of the second embodiment. FIG. 14 is a block diagram showing an electrical configuration of main parts of the endoscope and the processor in the endoscope system of the second embodiment.

A rigid distal end portion 106 is disposed closest to the distal end side of the insertion portion 4 in the endoscope system of the second embodiment.

As shown in FIG. 12, a cylindrical portion 140 in a columnar shape provided to protrude from a position above a center of a distal end surface of the distal end portion 106 is formed on the distal end portion 106 of the insertion portion 4.

An objective optical system not shown for both of the forward field of view and the lateral field of view is provided in a distal end portion of the cylindrical portion 140. The distal end portion of the cylindrical portion 140 includes: a forward observation window 111a arranged at a place equivalent to a forward direction of the objective optical system not shown; and a lateral observation window 111b arranged at a place equivalent to a lateral direction of the objective optical system not shown. A lateral illumination section 144 configured to emit light for illuminating the lateral direction is also formed near a proximal end of the cylindrical portion 140.

The lateral observation window 111b includes a lateral mirror lens 145 for enabling to acquire a lateral field of view image by capturing, in the lateral field of view, return light (reflected light) from the object to be observed, the return light entering from a circumferential direction of the cylindrical portion 140 in a columnar shape.

Note that an image pickup device 115 (image pickup surface of the image pickup device 115) shown in FIG. 14 is arranged on an image formation position of the objective optical system not shown, such that an image of the objective to be observed in the field of view of the forward observation window 111a is formed on a center portion as a circular forward field of view image, and an image of the object to be observed in the field of view of the lateral observation window 111b is formed on a circumference portion of the forward field of view image as an annular lateral field of view image.

The images are realized by using a twice-reflection optical system in which a side-view mirror lens reflects the return light twice. However, a once-reflection optical system may reflect the return light once to form the images, and the video processor 32 may apply image processing to the images to adjust the directions of the side-view field of view image and the front-view field of view image.

The distal end surface of the distal end portion 106 in the present second embodiment is provided with: a forward illuminating window 146 arranged at a position adjacent to the cylindrical portion 140 and configured to emit illuminating light to a range of the forward field of view of the forward observation window 111a; and a distal end opening portion 147 communicating with a treatment instrument channel not shown formed by a tube and the like disposed in the insertion portion 4, the distal end opening portion 147 capable of causing a treatment instrument (distal end portion of the treatment instrument) inserted into the treatment instrument channel to protrude.

The distal end portion 106 also includes a support portion 148 provided to protrude from the distal end surface of the distal end portion 106, and the support portion 148 is positioned on a lower side of the cylindrical portion 140, adjacent to the cylindrical portion 140.

The support portion 148 is configured to be able to support (or hold) each of protrusion members arranged to protrude from the distal end surface of the distal end portion 106. More specifically, the support portion 148 is configured to be able to support (or hold) each of the protrusion members, the protrusion members including: a forward observation window nozzle portion 149 configured to inject air or liquid for cleaning the forward observation window 111a; a forward illuminating window 151 configured to emit light for illuminating the forward direction; and lateral observation window nozzle portions 152 configured to inject air or liquid for cleaning the lateral observation window 111b.

On the other hand, the support portion 148 is formed by including a shield portion 148a that is an optical shield member configured to prevent each of the protrusion members that are objects different from the original object to be observed from appearing in the lateral field of view, thereby preventing acquisition of a lateral field of view image including one of the respective protrusion members.

Figure 15:
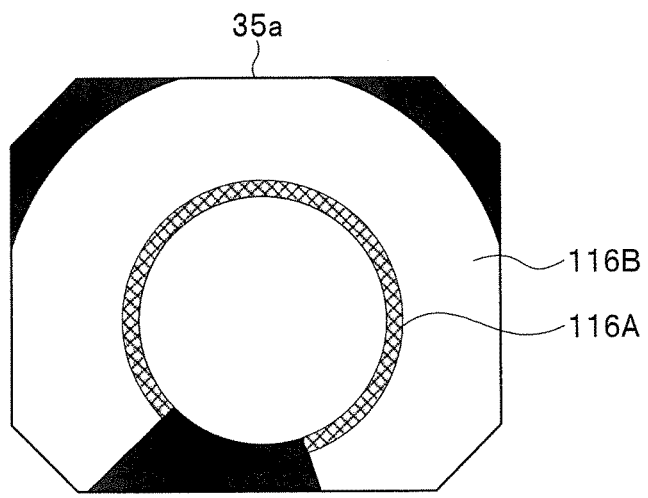
FIG. 15 is a diagram showing an outline of observation images displayed on the monitor screen in the endoscope system of the second embodiment.

That is, providing the shield portion 148a on the support portion 148 can obtain a lateral field of view image not including any of the forward observation window nozzle portion 149, the forward illuminating window 151, and the lateral observation window nozzle portions 152 (see FIG. 15).

The lateral observation window nozzle portions 152 are provided at two places of the support portion 148 as shown in FIGS. 12 and 13 and are arranged such that distal ends protrude from a side surface of the support portion 148.

The video processor 32 in the present second embodiment outputs a drive signal for driving the image pickup device 115 provided on the distal end portion 106 of the endoscope 102. The video processor 32 applies image processing to the image pickup signal outputted from the image pickup device 115 to generate a video signal and outputs the video signal to the monitor 35.

As a result, observation images including a forward field of view image in a circular shape and a lateral field of view image in an annular shape on a circumference of the image in the forward direction are displayed on the monitor screen 35a (details will be described later).

Note that the part optically shielded by the shield portion 148a of the support portion 148 is not taken into account in the observation images illustrated in the present second embodiment.

For example, the depth perception and the three-dimensional effect cannot be obtained just by arranging one or more lateral field of view images next to the forward field of view image, and it is difficult to recognize the images as images for observing inside of a lumen without unnatural feeling.

On the other hand, the screen radially spreads from the center toward the surrounding in an optical structure set in a display method of the forward field of view image and the lateral field of view images in the endoscope system of the present second embodiment (an annular lens automatically provides such optical characteristics). Therefore, the depth perception and the three-dimensional effect can be relatively easily obtained.

Next, main parts of an electrical configuration in the endoscope system of the present second embodiment will be described.

FIG. 14 is a block diagram showing main parts of an electrical configuration of the endoscope and the processor in the endoscope system of the second embodiment.

As shown in FIG. 14, the forward observation window 111a, the lateral observation window 111b, and the image pickup device 115 are disposed on the distal end portion of the cylindrical portion 140 in the distal end portion 106 of the insertion portion 4 of the endoscope 102 in the present second embodiment.

Note that in the present second embodiment, the forward observation window 111a forms a first subject image acquisition section. The lateral observation window 111b forms a second subject image acquisition section. The image pickup device 115 forms both of the first subject image acquisition section and the second subject image acquisition section.

As in the first embodiment, the forward observation window 111a receives (observes) a first subject image from the forward direction, that is, the front-view direction (first region in which left side in FIG. 14 is forward), wherein the direction in which the insertion portion 4 is inserted that is substantially parallel to the longitudinal axis direction of the insertion portion 4 is the forward direction.

The lateral observation window 111b receives (observes) a second subject image from a lateral direction that is a direction different from the forward direction (first direction) and that includes a circumferential direction intersecting with the longitudinal axis direction of the insertion portion 4 of the distal end portion 106, that is, a side-view direction (second region).

As described, the image pickup surface of the image pickup device 115 is arranged, such that an image of the object to be observed in the field of view of the forward observation window 111a (first subject image) is formed on the center portion as a circular forward field of view image on the monitor screen 35a, and an image of the object to be observed in the field of view of the lateral observation window 111b (second subject image) is formed as an annular lateral field of view image on the circumference portion of the forward field of view image, next to the forward field of view image. The image pickup device 115 photoelectrically converts the first subject image and the second subject image.

The image pickup device 115 is electrically connected to the image signal generation section 32g and is configured to output the image pickup signals related to the forward field of view and the lateral field of view picked up by the image pickup device 115 to the image signal generation section 32g in the video processor 32.

In the present second embodiment, the scope ID 29a storing, for example, view angle information as unique predetermined ID information in the endoscope 102 is also disposed on the connector 29 in the endoscope 102.

As in the first embodiment, the video processor 32 in the present second embodiment also outputs a drive signal for driving the image pickup device 115 and includes: the image signal generation section (first image signal generation section) 32g configured to receive the image pickup signals from the image pickup devices 115 to generate video signals (image signals) related to the forward or lateral field of view; the image processing section 32a configured to apply predetermined image processing to the video signals (image signals); the image output section 32b configured to apply predetermined processing to the respective image signals processed by the image processing section 32a to generate output image signals to be outputted to the monitor 35 and output the output image signals; and the auxiliary image generation section (second image signal generation section) 32c configured to acquire the unique information in the endoscope 102 from the scope ID 29a in the connector 29 to generate a predetermined auxiliary image described later.

Next, image processing by the image processing section 32a and the auxiliary image generation section 32c in the present second embodiment will be described with reference to FIGS. 15 and 16.

FIG. 15 is a diagram showing an outline of observation images displayed on the monitor screen in the endoscope system of the second embodiment. FIG. 16 is a diagram showing an example of observation images displayed on the monitor screen in the endoscope system of the second embodiment.

In the second embodiment, as shown in FIG. 15, the image signal generation section 32g receives an image pickup signal based on the subject image of the forward field of view obtained by the first subject image acquisition section (the forward observation window 111a, the image pickup device 115, and the like) and an image pickup signal based on the subject image of the lateral field of view obtained by the second subject image acquisition section (the lateral observation window 111b, the image pickup device 115, and the like) to generate image signals.

Figure 16:
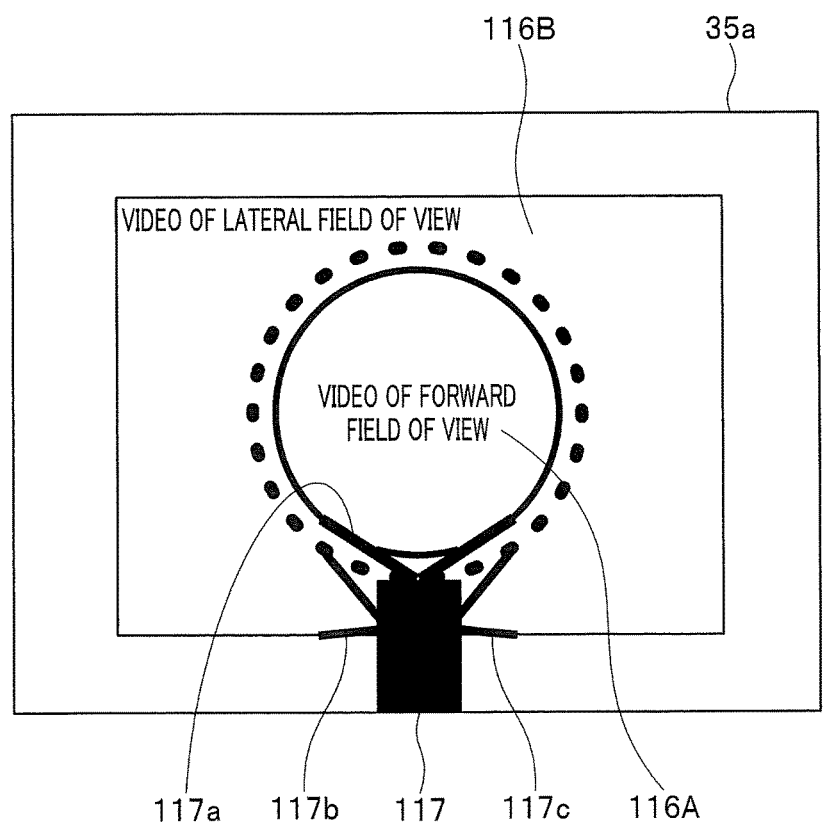
FIG. 16 is a diagram showing an example of observation images displayed on the monitor screen in the endoscope system of the second embodiment.

Based on the image signals, as shown in FIGS. 15 and 16, the image processing section 32a applies predetermined processing to arrange, in a circular shape, a forward field of view image 116A based on the subject image of the forward field of view from the first subject image acquisition section, at the center in the monitor screen 35a of the monitor 35, and arrange, in an annular shape, a lateral field of view image 116B based on the subject image of the lateral field of view from the second subject image acquisition section, adjacent to the forward field of view image 16A and on the circumference portion of the forward field of view image 16A. The image processing section 32a outputs the images to the image output section 32b.

Note that in the present second embodiment, the lateral field of view image 116B includes a shield portion 116C optically shielded by the shield portion 148a.

Subsequently, the image processing section 32a outputs image signals (first image signals) regarding the forward field of view image 116A and the lateral field of view image 116B generated in the procedure described above toward the image output section 32b.

On the other hand, as shown in FIG. 16, the auxiliary image generation section 32c reads the view angle information as the unique ID information in the endoscope 102 stored in the scope ID 29a disposed on the connector 29 and generates a bird's-eye view image 117 based on the read view angle information. The auxiliary image generation section 32c applies processing to arrange and display the bird's-eye view image 117 on the shield portion 116C in the monitor screen 35a.

As in the first embodiment, the bird's-eye view image 117 is a bird's-eye view subject image, looking down on the subject from a virtual point of view away from the insertion portion 4 (for example, a point on an upper part of the endoscope insertion portion).

In the present second embodiment, the bird's-eye view image 117 includes a bird's-eye view forward field of view line 117a indicating a bird's-eye view forward field of view range and bird's-eye view lateral field of view lines 117b and 117c indicating bird's-eye view lateral field of view ranges that are schematic diagrams respectively indicating forward or two lateral view angles. The auxiliary image generation section 32c generates the lines based on the view angle information in the endoscope 102 stored in the scope ID 29a.

A line indicating the field of view range of the bird's-eye view forward field of view line 117a touches and intersects with a peripheral part of the forward field of view image 116A, and the bird's-eye view forward field of view line 117a is associated as if the forward field of view image 116A is on an extension of the bird's-eye view forward field of view range.

Similarly, lines indicating the field of view ranges of the bird's-eye view lateral field of view lines 117b and 117c intersect with part of the lateral field of view image 116B, and the bird's-eye view lateral field of view lines 117b and 117c are associated as if the lateral field of view image 116B is on an extension of the bird's-eye view lateral field of view ranges.

The auxiliary image generation section 32c generates the bird's-eye view image 117 in the procedure described above, generates an image signal (second image signal) regarding the bird's-eye view image 117, and outputs the image signal toward the image processing section 32a.

The image processing section 32a synthesizes the image signals based on the image signals (first image signals) generated by the image signal generation section 32g and the image signal (second image signal) generated by the auxiliary image generation section 32c and outputs the signals to the image output section 32b. The image output section 32b generates an output image signal for display on the monitor screen 35a and outputs the output image signal toward the monitor 35.

In this way, in the present second embodiment, the states of array of the "forward field of view image" and the "bird's-eye view forward field of view range" as well as the "lateral field of view images" and the "bird's-eye view lateral field of view ranges" are "associated" and displayed in the same procedure as in the first embodiment.

As, described, as in the first embodiment, the endoscope system of the present second embodiment attains an effect of allowing to provide an endoscope system capable of independently and simultaneously observing the forward field of view and the lateral field of view, the endoscope system being capable of distinguishing and displaying the forward field of view image and the lateral field of view images and accurately recognizing the directions and the ranges in the subject that the forward field of view image and the lateral field of view images correspond.

First Modification of Second Embodiment

Next, a first modification of the present second embodiment will be described.

Figure 17:
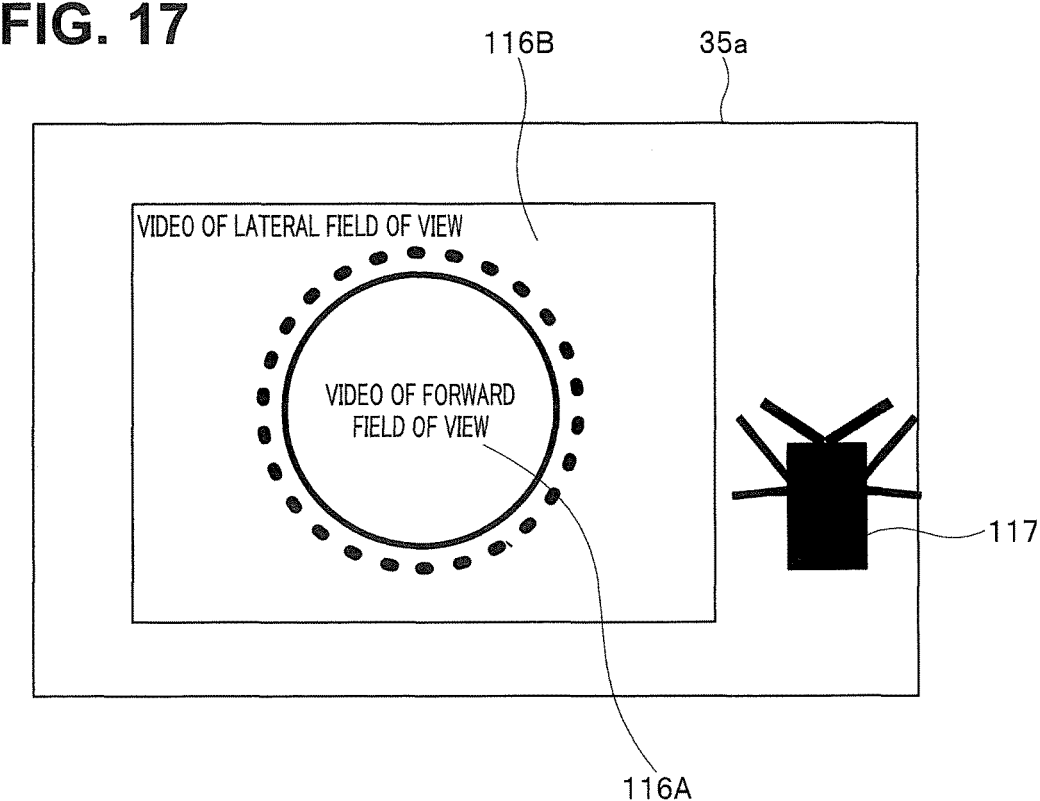
FIG. 17 is a diagram showing an example of observation images displayed on the monitor screen in a first modification of the endoscope system of the second embodiment.

FIG. 17 is a diagram showing an example of observation images displayed on the monitor screen in the first modification of the endoscope system of the second embodiment.

In the second embodiment described above, the bird's-eye view image 117 is positioned in the region of the shield portion 116C below the forward field of view image 116A and the lateral field of view image 116B, and the bird's-eye view forward field of view line 117a and the bird's-eye view lateral field of view lines 117b and 117c are closely associated with the forward field of view image 116A and the lateral field of view image 116B, respectively. The bird's-eye view image 117 is displayed as if the bird's-eye view image 117 is displayed on the extension of the bird's-eye view field of view range.

However, the arrangement position of the bird's-eye view image 117 is not limited to this. For example, as in the first modification of the second embodiment, the bird's-eye view image 117 may be arranged outside of the display region of the endoscopic image in the monitor screen 35a (for example, close to the side surface of the lateral field of view image 116B).

Second Modification of Second Embodiment

Next, a second modification of the present second embodiment will be described.

Figure 18:
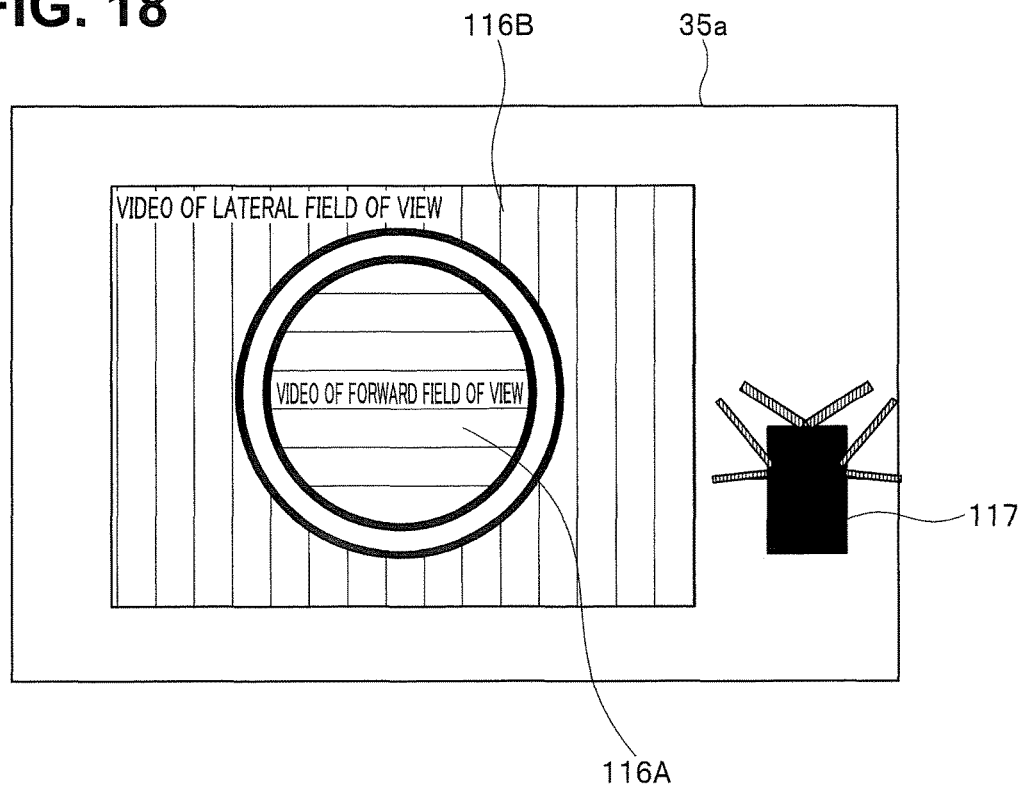
FIG. 18 is a diagram showing an example of observation images displayed on the monitor screen in a second modification of the endoscope system of the second embodiment.

FIG. 18 is a diagram showing an example of observation images displayed on the monitor screen in the second modification of the endoscope system of the second embodiment.

In the second embodiment or the first modification of the second embodiment, the bird's-eye view forward field of view line 117a and the bird's-eye view lateral field of view lines 117b and 117c may be displayed by "using different colors" as in the first embodiment.

In this case, the forward field of view image 116A and the lateral field of view image 116B may also be associated and displayed by "using different colors" as shown in FIG. 18.

Obviously, the forward field of view image 116A and the lateral field of view image 116B may be associated not only by "using different colors", but also by "using different patterns with contour lines" or "using different patterns with symbols" as in the first embodiment, the second modification of the first embodiment, and the third modification of the first embodiment.

Third Modification of Second Embodiment

Next, a third modification of the present second embodiment will be described.

Figure 19:
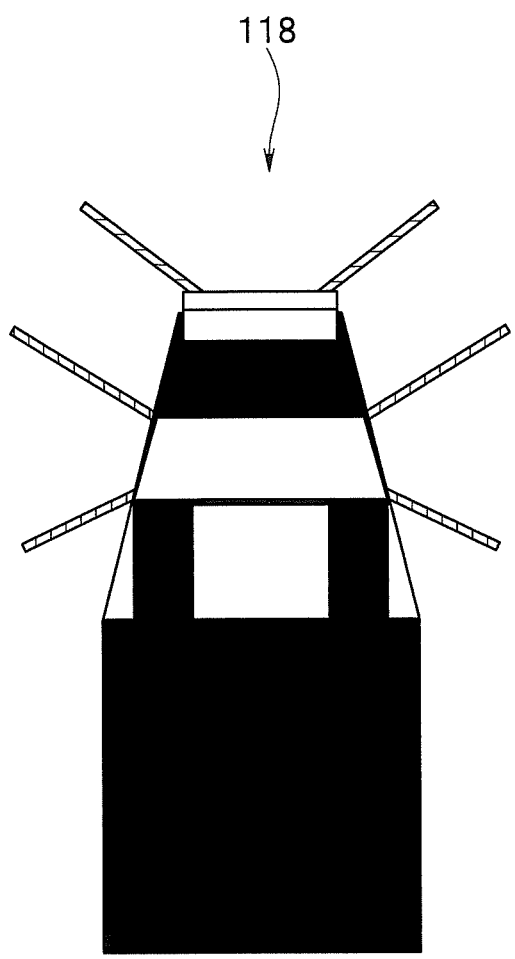
FIG. 19 is a diagram showing an example of observation images displayed on the monitor screen in a third modification of the endoscope system of the second embodiment.

FIG. 19 is a diagram showing an example of a bird's-eye view image displayed on the monitor screen in the third modification of the endoscope system of the second embodiment.

In the second embodiment or the first or second modification of the second embodiment, the part of the schematic diagram of the endoscope in the bird's-eye view image 117 may be displayed as a bird's-eye view image 118 resembling the shape of the actual endoscope as in FIG. 19.

Fourth Modification of Second Embodiment

Next, a fourth modification of the present second embodiment will be described.

Figure 20:
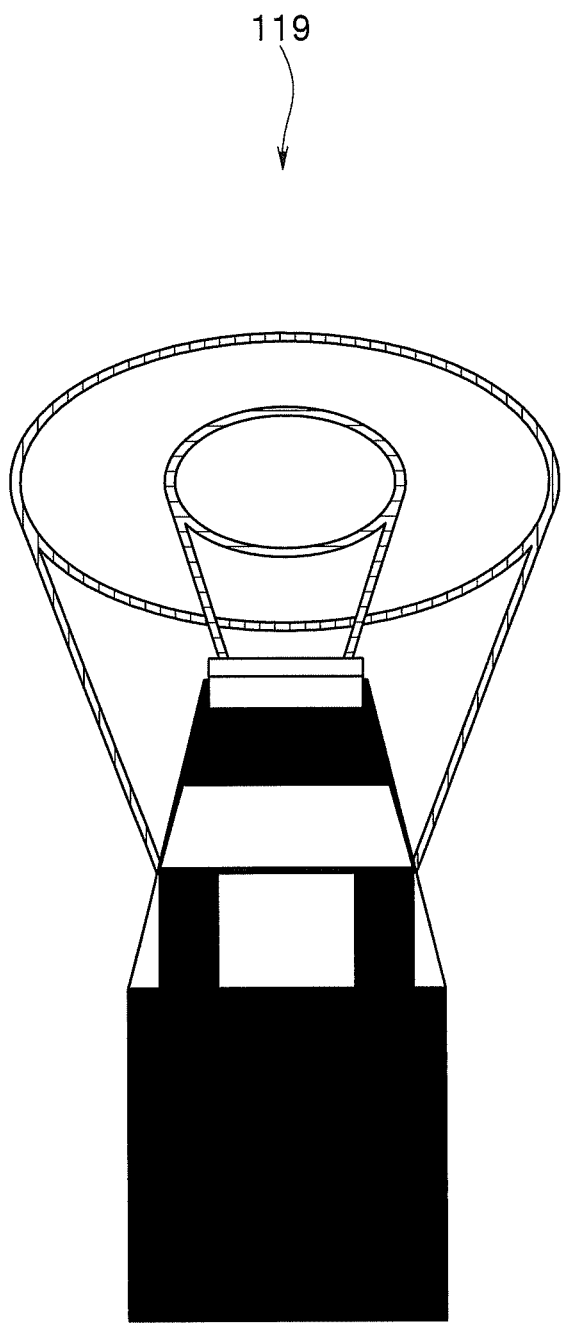
FIG. 20 is a diagram showing an example of observation images displayed on the monitor screen in a fourth modification of the endoscope system of the second embodiment.

FIG. 20 is a diagram showing an example of a bird's-eye view image displayed on the monitor screen in the fourth modification of the endoscope system of the second embodiment.

In the first and second modifications of the second embodiment, the schematic part of the endoscope in the bird's-eye view image 117 may be displayed as a bird's-eye view image 119 as if the forward field of view image and the lateral field of view images are projected.

An actual endoscopic image may also be displayed at the part of the projected location resembling the forward field of view image and the lateral field of view images in the bird's-eye view image 119 in the modification.

Third Embodiment

Next, a third embodiment of the present invention will be described.

The basic configuration of the endoscope system of the present third embodiment of the present invention is similar to that of the first embodiment including the schematic configuration of the distal end portion 6 in the endoscope 2. However, the endoscope system is different from that of the first embodiment in that the endoscope system includes shape detection means of the endoscope insertion portion, and the type of the bird's-eye view image is different.

Therefore, only the part different from the first embodiment will be described here, and the same part as in the first embodiment will not be described.

Figure 21:
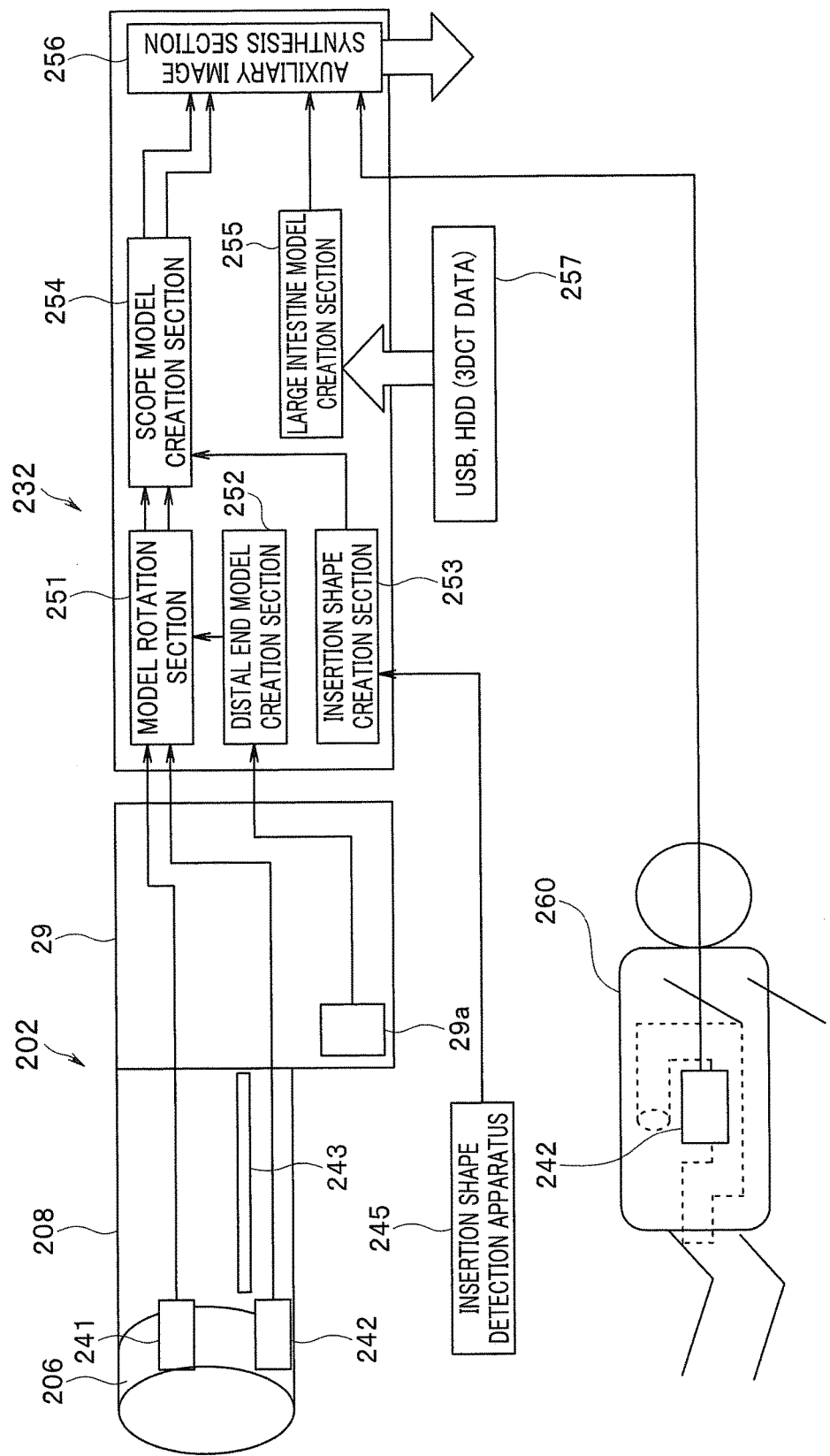
FIG. 21 is a block diagram showing an electrical configuration of main parts in an endoscope system of a third embodiment of the present invention.

FIG. 21 is a block diagram showing an electrical configuration of main parts of an endoscope and a processor in the endoscope system of the third embodiment of the present invention.

As in the first embodiment, an endoscope system 201 of the present third embodiment includes: an endoscope 202 configured to pick up an image of an object to be observed and output an image pickup signal; the light source apparatus 31 configured to supply illuminating light for illuminating the object to be observed; a video processor 232 configured to generate and output a video signal according to the image pickup signal; and the monitor 35 configured to display an observation image according to the video signal.

As in the first embodiment, the forward observation window 11a and the forward image pickup device 15a forming the first subject image acquisition section as well as the lateral observation windows 11b and 11c and the lateral image pickup devices 15b and 15c forming the second subject image acquisition section are disposed on an insertion portion distal end portion 206 of the endoscope 202 in the endoscope system of the third embodiment, although not shown in FIG. 21.

The endoscope 202 also includes: a rotation sensor 241 configured to detect rotation of an insertion portion near a distal end portion of the endoscope 202; a gravity sensor 242 configured to detect an insertion direction of the insertion portion; and a magnetic sensor 243 configured to detect an insertion shape of an insertion portion 208.

In the endoscope system, an insertion shape detection apparatus 245 configured to detect the insertion shape of the insertion portion 208 along with the magnetic sensor 243 is provided outside of the endoscope 202. Note that reference sign 260 in FIG. 21 indicates a subject.

On the other hand, as in the first embodiment, the video processor 232 in the endoscope system of the third embodiment includes, although not shown in FIG. 21: the image signal generation section 32g configured to generate an image signal by receiving the image pickup signals from the forward observation window 11a and the forward image pickup device 15a forming the first subject image acquisition section for observing the forward direction and the image pickup signals from the lateral observation windows 11b and 11c and the lateral image pickup devices 15b and 15c forming the second subject image acquisition section for observing the lateral direction; the image processing section 32a configured to output drive signals for driving the forward image pickup devices 15a, 15b, and 15c and to receive the image signal from the image signal generation section 32g to apply predetermined image processing to the image signal; and the image output section 32b configured to apply predetermined processing to the image signal processed by the image processing section 32a to generate an output image signal to be outputted to the monitor 35 and output the output image signal.

The video processor 232 in the present third embodiment also includes: a distal end model creation section 252 configured to acquire unique information in the endoscope 202 from the scope ID 29a in the connector 29 to generate a 3D distal end model including a predetermined bird's-eye view field of view range image; a model rotation section 251 configured to receive detection information of the rotation sensor 241 and the gravity sensor 242 to apply predetermined operation to the distal end model created by the distal end model creation section 252; an insertion shape creation section 253 configured to receive the insertion shape information detected by the magnetic sensor 243 and the insertion shape detection apparatus 245 to calculate an insertion shape; a large intestine model creation section 255 configured to acquire 3DCT data through a USB not shown or recorded in an HDD or the like to create a large intestine model of the subject; a scope model creation section 254 configured to create a scope model based on operation results of the model rotation section 251 and the insertion shape creation section 253; and an auxiliary image synthesis section 256 configured to synthesize image signals from the scope model creation section 254 and the large intestine model creation section 255 to generate an auxiliary image.

Next, image processing by the video processor 232 in the present third embodiment will be described with reference to FIGS. 21, 22 to 24a, 24b, and 24c.

Figure 22:
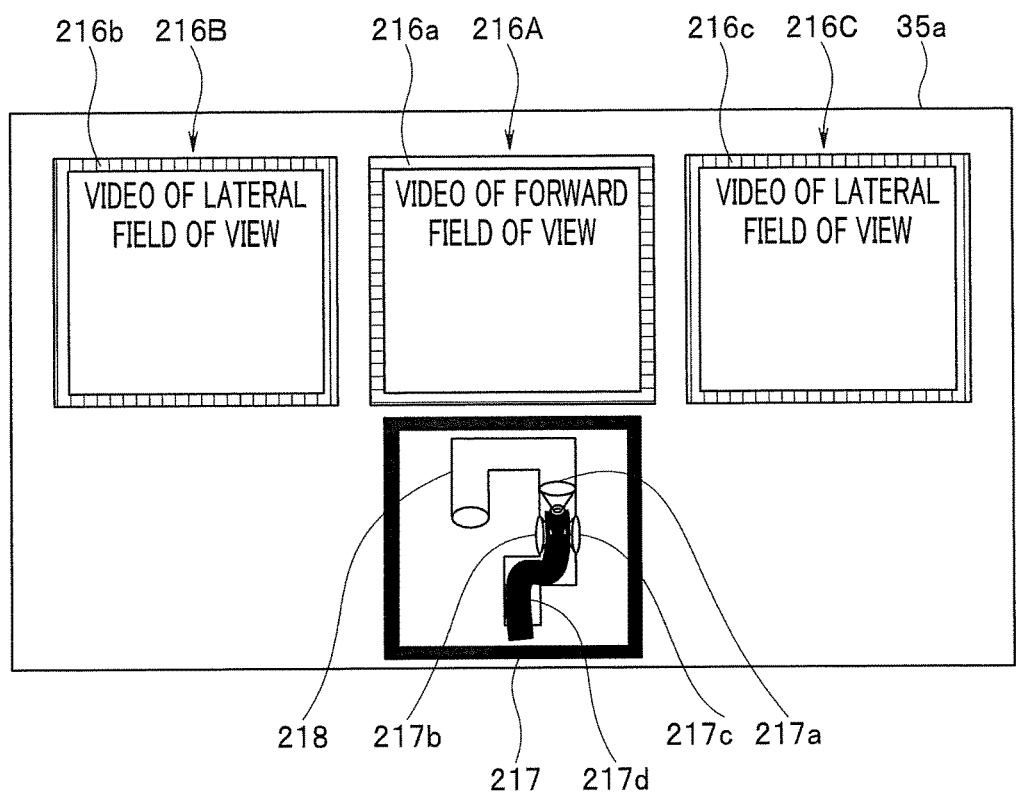
FIG. 22 is a diagram showing an example of observation images displayed on the monitor screen in the endoscope system of the third embodiment.
Figure 23A:
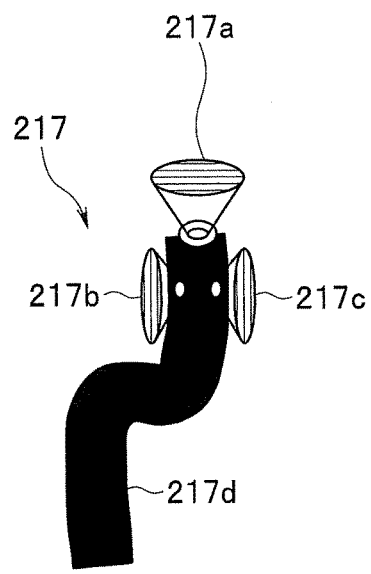
FIG. 23a is a diagram showing details of an example of constituent elements of a bird's-eye view displayed on the monitor screen in the endoscope system of the third embodiment.
Figure 23B:
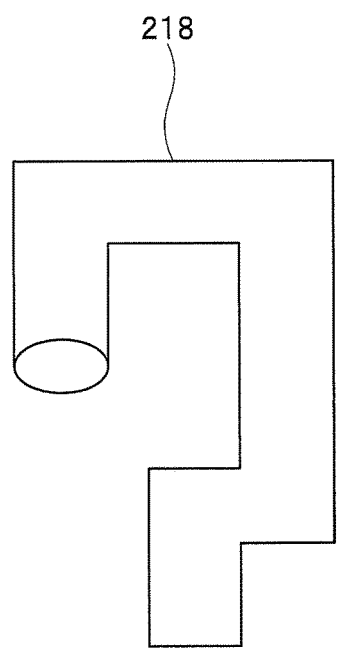
FIG. 23b is a diagram showing details of an example of constituent elements of a bird's-eye view displayed on the monitor screen in the endoscope system of the third embodiment.
Figure 24A:
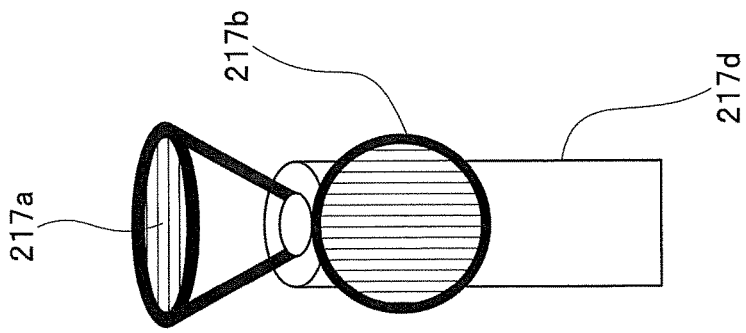
FIG. 24a is a diagram showing an action of the constituent elements of the bird's-eye view displayed on the monitor screen in the endoscope system of the third embodiment.
Figure 24B:
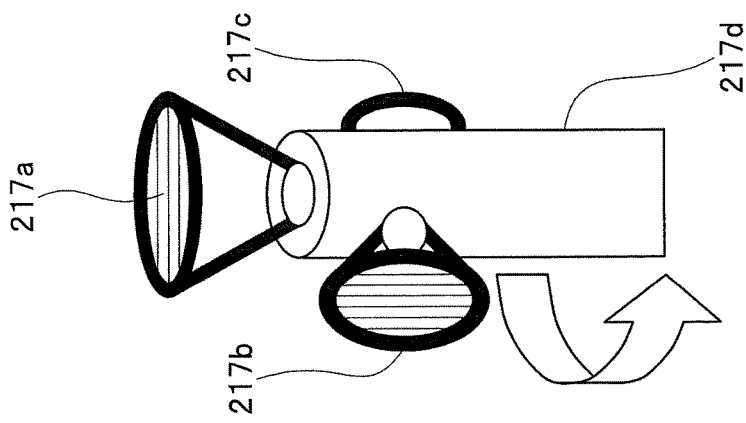
FIG. 24b is a diagram showing an action of the constituent elements of the bird's-eye view displayed on the monitor screen in the endoscope system of the third embodiment.
Figure 24C:
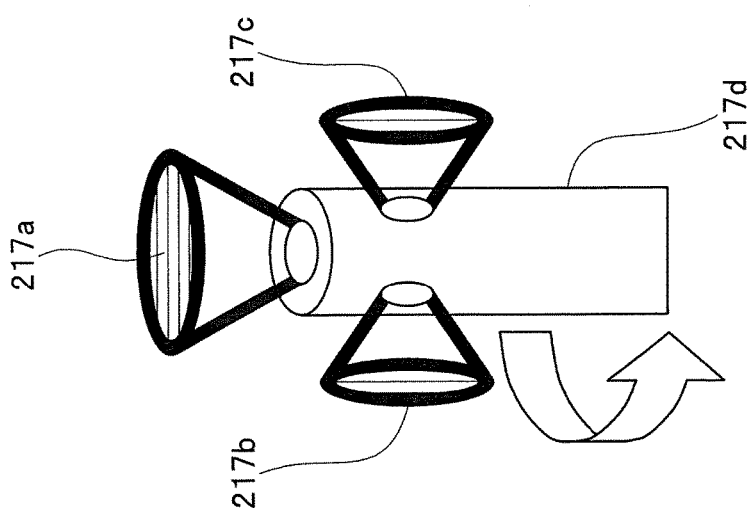
FIG. 24c is a diagram showing an action of the constituent elements of the bird's-eye view displayed on the monitor screen in the endoscope system of the third embodiment.

FIG. 22 is a diagram showing an example of observation images displayed on the monitor screen in the endoscope system of the third embodiment. FIGS. 23a and 23b are diagrams showing details of an example of constituent elements of a bird's-eye view displayed on the monitor screen in the endoscope system of the third embodiment. FIGS. 24a, 24b and 24c are diagrams showing actions of the constituent elements of the bird's-eye view displayed on the monitor screen in the endoscope system of the third embodiment.

First, the magnetic sensor 243 is inserted into the insertion portion 208, and the magnetic sensor 243 and the insertion shape detection apparatus 245 detect the insertion shape of the insertion portion 208.

Subsequently, the insertion shape creation section 253 in the video processor 232 acquires the detection result information of the insertion shape and creates an insertion shape of the insertion portion 208.

On the other hand, the distal end model creation section 252 acquires the field of view information regarding the endoscope 202 from the scope ID 29a and uses the same method as in the first embodiment to create data of a distal end model 217 including a bird's-eye view forward field of view range 217a, bird's-eye view lateral field of view ranges 217b and 217c, and a bird's-eye view insertion portion 217d (see FIG. 23a).

Note that in the present third embodiment, the distal end model creation section 252 is configured to create the distal end model including the bird's-eye view forward field of view range 217a, the bird's-eye view lateral field of view ranges 217b and 217c, and the bird's-eye view insertion portion 217d as a 3D model (see FIGS. 24a, 24b, and 24c).

Next, the model rotation section 251 in the video processor 232 receives the detection information of the rotation sensor 241 and the gravity sensor 242 and takes into account information such as rotation to apply predetermined operation to the 3D distal end model created by the distal end model creation section 252 to output the 3D distal end model.

The scope model creation section 254 creates the distal end model 217 as a scope model at the point based on the operation results of the model rotation section 251 and the insertion shape creation section 253 (see FIG. 23a).

On the other hand, the large intestine model creation section 255 acquires the 3DCT data through a USB not shown or recorded in an HDD or the like to create a large intestine model 218 of the subject (see FIG. 23b).

Subsequently, the auxiliary image synthesis section 256 synthesizes the distal end model 217 (FIG. 23a) at the point created by the scope model creation section 254 and the large intestine model 218 (FIG. 23b) of the subject created by the large intestine model creation section 255 to generate an auxiliary image and displays the auxiliary image at a place where the bird's-eye view image 17 is arranged in the monitor screen 35a (see FIG. 22).

Note that although the distal end model 217 (FIG. 23a) and the large intestine model 218 of the subject (FIG. 23b) are synthesized to generate the auxiliary image in the present third embodiment, one of the model images may be displayed at the place where the bird's-eye view image 17 is arranged.

As described, as in the first embodiment, the endoscope system of the present third embodiment can independently and simultaneously observe the forward field of view and the lateral field of view, the endoscope system being capable of distinguishing and displaying the forward field of view image and the lateral field of view images and accurately recognizing the directions and the ranges in the subject that the forward field of view image and the lateral field of view images correspond.

First Modification of Third Embodiment

Next, a first modification of the present third embodiment will be described.

Figure 25:
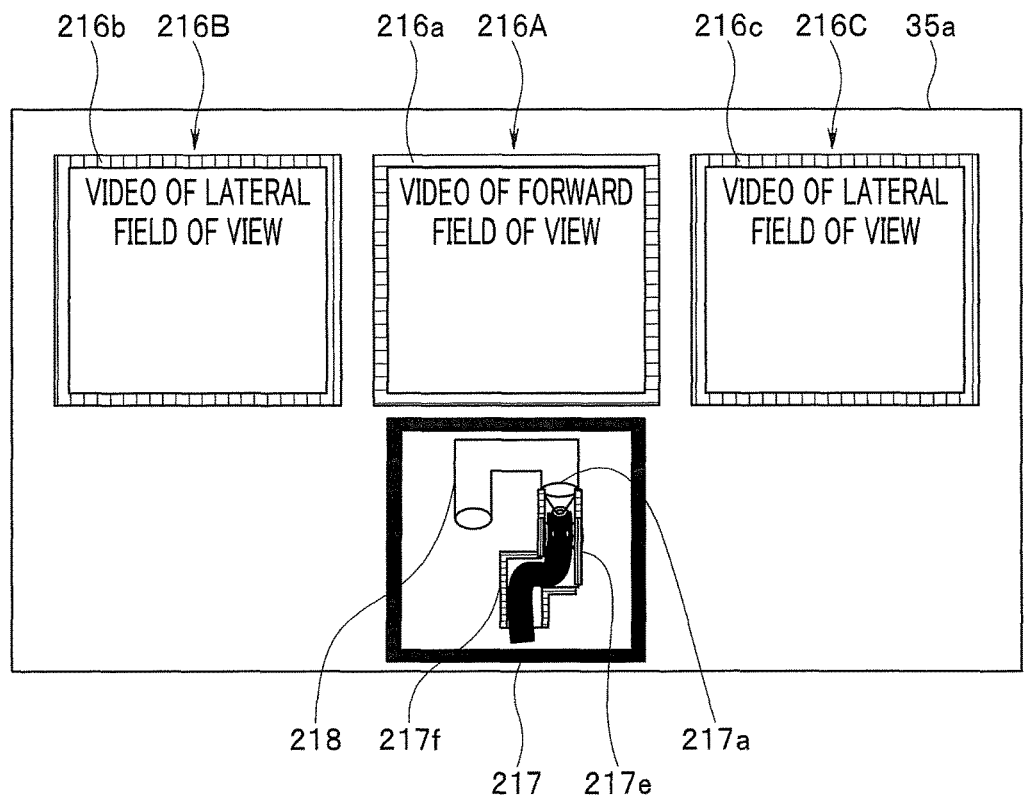
FIG. 25 is a diagram showing an example of observation images displayed on the monitor screen in a first modification of the endoscope system of the third embodiment.
Figure 26:
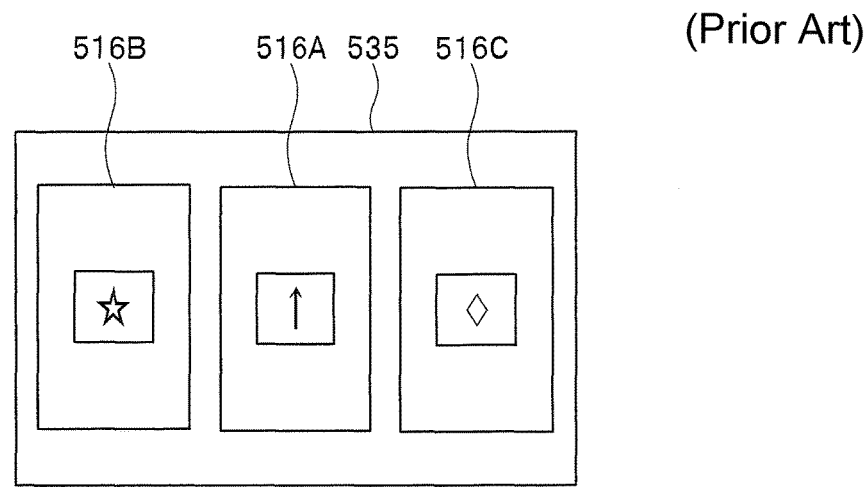
FIG. 26 is a diagram showing an example of observation images displayed on a monitor screen in a conventional endoscope system.
Figure 27A:
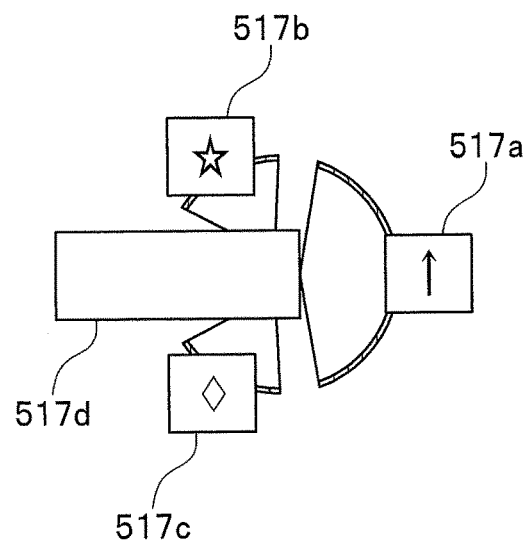
FIG. 27a is a diagram for describing directions and positions actually observed in the conventional endoscope system shown in FIG. 26.
Figure 27B:
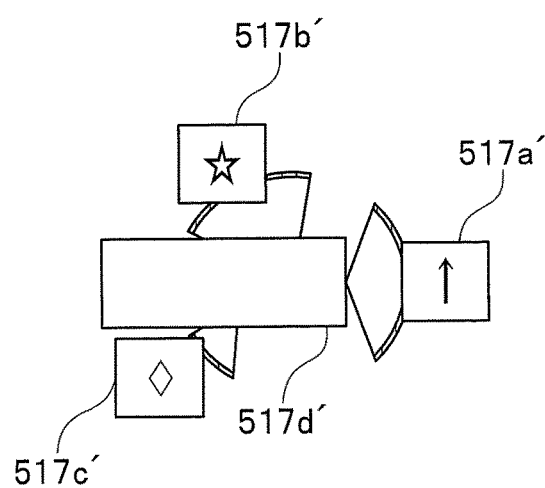
FIG. 27b is a diagram for describing directions and positions actually observed in the conventional endoscope system shown in FIG. 26.
Figure 28:
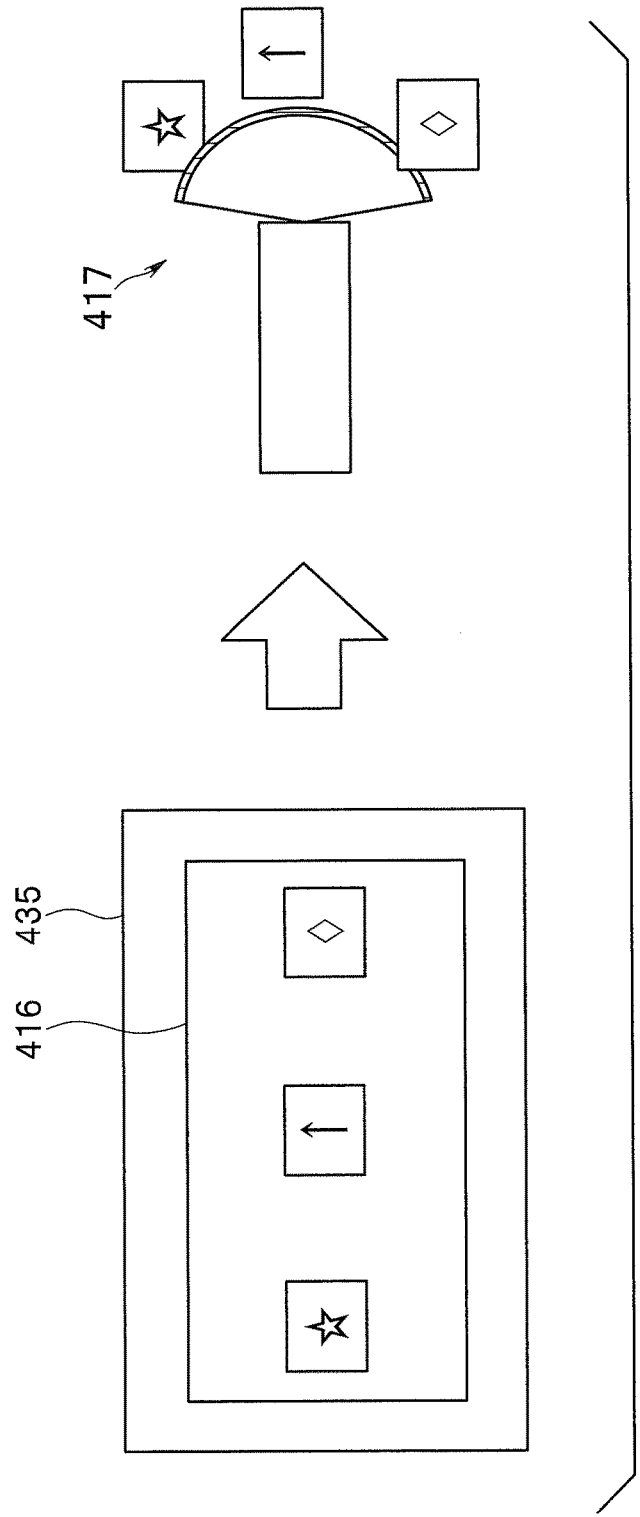
FIG. 28 is a diagram for describing an example of observation images displayed on the monitor screen and directions and positions actually observed in the conventional endoscope system.

FIG. 25 is a diagram showing an example of observation images displayed on the monitor screen in the first modification of the endoscope system of the third embodiment.

In the auxiliary image of the third embodiment, the forward field of view image and the lateral field of view images as well as the bird's-eye view forward field of view range and the bird's-eye view lateral field of view ranges may be associated by "using different colors" as in the first embodiment.

Note that although the lateral field of view images 16B and 16C are arranged on the left and right of the forward field of view image 16A when a plurality of images are displayed on the monitor screen 35a in the first and third embodiments, the arrangement is not limited to the arrangement. Two lateral field of view images may be arranged on one of the left and the right of the forward field of view image 16A.

Although a plurality of images are displayed on one monitor screen 35a in one monitor 35 in the present first to third embodiments, the display is not limited to the display. For example, a plurality of monitors may be arranged adjacent to each other. The forward field of view image may be displayed on a center monitor, and the respective lateral field of view images may be displayed on left and right monitors.

According to the endoscope system of the present invention, the forward field of view and the lateral field of view can be independently and simultaneously observed. The forward field of view image and the lateral field of view images can be distinguished and displayed, and the directions and the ranges in the subject that the forward field of view image and the lateral field of view images correspond can be accurately recognized.

The present invention is not limited to the embodiments, and various changes, modifications, and the like can be made within a range not changing the scope of the present invention.

What is claimed is:

1. An endoscope system comprising:
   an insertion portion inserted into a subject in a longitudinal axis direction;
   a first image sensor configured to acquire a first subject image corresponding to a first region of the subject and generate a first electrical signal based on the acquired first subject image;
   a first observation window provided on the insertion portion and configured to transmit the first subject image to the first image sensor;
   a second image sensor configured to acquire a second subject image corresponding to a second region of the subject different from the first region and generate a second electrical signal based on the acquired second subject image;
   a second observation window provided on the insertion portion and configured to transmit the second subject image to the second image sensor;
   a processor including hardware, the processor being configured to:
      generate a first image signal based on the first electrical signal, the first image signal corresponding to an endoscopic subject image including the first subject image and the second subject image;
      generate a second image signal based on the second electrical signal, the second image signal corresponding to a schematic diagram of the insertion portion and an array of the first and second regions relative to the insertion portion;
      associate the first subject image and the first region with respect to the schematic diagram of the insertion portion;
      associate the second subject image and the second region with respect to the schematic diagram of the insertion portion;
      synthesize the first and second image signals to arrange the associated first subject image and the associated second subject image on a screen; and
      generate an output image signal for display on the screen based on the first and second image signals synthesized,
   wherein the insertion portion comprises one or more sensors detecting a shape or a rotation state of the insertion portion, and
   wherein the processor is further configured to generate the schematic diagram of the insertion portion indicating a state that the insertion portion is inserted into a lumen of the subject in the second image signal based on information provided from the one or more sensors.

2. The endoscope system according to claim 1, wherein the one or more sensors comprise a magnetic sensor detecting the shape of the insertion portion.

3. The endoscope system according to claim 2, wherein the processor is further configured to:
   generate a three-dimensional image of the lumen of the subject; and
generate the schematic diagram of the insertion portion indicating the state that the insertion portion is inserted into the lumen of the subject in the second image signal further based on information provided from the generated three-dimensional image of the lumen of the subject.

4. The endoscope system according to claim 1, wherein
   the first subject image is a subject image of the first region including a region in front of the insertion portion substantially parallel to a longitudinal direction of the insertion portion,
   the second subject image is a subject image of the second region including a region by the side of the insertion portion in a direction intersecting with the longitudinal direction of the insertion portion.

5. The endoscope system according to claim 1, wherein
   the first observation window is arranged on a distal end portion in a longitudinal direction of the insertion portion and arranged in a direction in which the insertion portion is inserted,
   the second observation window is arranged on a side surface of the insertion portion and arranged in a circumferential direction of the insertion portion,
   the first image sensor is configured to photoelectrically convert the first subject image provided from the first observation window to the first electrical signal,
   the second image sensor is configured to photoelectrically convert the second subject image provided from the second observation window to the second electrical signal, and
   the first image sensor and the second image sensor are separately provided, and electrically connected to at least the processor.

6. The endoscope system according to claim 5, further comprising:
   a third observation window provided on the insertion portion and configured to transmit a third subject image to an image sensor, the third subject image corresponding to a third region of the subject different from the first region and the second region,
   wherein the second observation window and the third observation window are arranged at substantially equal angles in the circumferential direction of the insertion portion, and
   the processor is further configured to generate one or more image signals, in which the first subject image is arranged at a center, and the second subject image and the third subject image are arranged at plural positions in the circumferential direction of the first subject image at substantially equal angles.

7. The endoscope system according to claim 1, wherein
   the first observation window is arranged on a distal end portion in a longitudinal direction of the insertion portion and arranged in a direction in which the insertion portion is inserted,
   the second observation window is arranged to surround a circumferential direction of the insertion portion,
   the first image sensor photoelectrically converts the first subject image provided from the first observation window to the first electrical signal, and the second image sensor photoelectrically converts the second subject image provided from the second observation window to the second electrical signal, and the first image sensor and the second image sensor are arranged to have a same surface, and are electrically connected to the processor.

8. The endoscope system according to claim 7, wherein the processor generates an image signal, in which the first subject image is in a substantially circular shape, and the second subject image is in an annular shape surrounding the first subject image.

* * * * *